US005910628A

United States Patent [19]

Miller et al.

[11] Patent Number: 5,910,628

[45] Date of Patent: Jun. 8, 1999

[54] CAP-INDEPENDENT TRANSLATION SEQUENCES DERIVED FROM BARLEY YELLOW DWARF VIRUS

[75] Inventors: W. Allen Miller, Ames, Iowa; Shanping Wang, Charlestown, Mass.

[73] Assignee: Iowa State University Research Foundation, Inc., Ames, Iowa

[21] Appl. No.: 08/858,623

[22] Filed: May 20, 1997

Related U.S. Application Data

[60] Provisional application No. 60/017,199, May 20, 1996.

[51] Int. Cl.$^6$ .......... A01H 1/04

[52] U.S. Cl. .......... 800/205; 435/69.1; 435/254.2; 435/410; 435/419; 536/24.1

[58] Field of Search .......... 435/69.1, 172.3, 435/320.1, 177.3, 254.2, 254.11, 410, 419; 536/24.1; 800/205

[56] References Cited

PUBLICATIONS

Wang et al. The Journal of Biological Chemistry. vol. 270 (22), pp. 13446–13452, Jun. 2, 1995.

*Primary Examiner*—James Ketter
*Assistant Examiner*—Irem Yucel
*Attorney, Agent, or Firm*—Benjamin Aaron Adler

[57] ABSTRACT

The present invention provides a method of increasing the production of a protein translated from an uncapped eukaryotic messenger ribonucleic acid (mRNA), comprising the steps of: selecting a nucleotide sequence encoding a protein to be expressed; joining nucleotides 1–168 of the barley yellow dwarf virus RNA, PAV serotype to the 5' untranslated region of said uncapped mRNA, said nucleotides 1–168 comprising the 5' untranslated region plus first 27 nucleotides of the open reading frame of the barley yellow dwarf virus RNA; linking nucleotides 4513–5677 of the barley yellow dwarf virus RNA, PAV serotype, to the 3' untranslated region of said uncapped mRNA; and expressing the protein. Also provided is a DNA molecule which comprises: (a) a promoter region which functions in plant cells to cause the production of an RNA sequence, which is operably linked to (b) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA; (c) a coding sequence, wherein said coding sequence is heterologous to said 5' untranslated region, which is operably linked to (d) a 3' untranslated region that functions in plant cells to cause the termination of transcription, said 3' untranslated region comprising nucleotides 4513–5677 of the barley yellow dwarf virus RNA.

15 Claims, 20 Drawing Sheets

| | nt from end of 3′ ORF | | nt to end of genome | Virus Group |
|---|---|---|---|---|
| PAV | - 14 - | gcacaaau**CGGAUCCUGGGAAACAGG**cagaacu | - 817 - | Luteo, Subgroup |
| MAV | - 15 - | gca.aaua**CGGAUCCUGGGAAACAGG**cagaacu | - 805 - | Luteo, Subgroup |
| SDV | - 61 - | gcugucgug**GGAUCCUGGGAAACAGG**uucgguG | - 558 - | Luteo, Subgroup |
| TNV-A | - 51 - | gacggaga**CGGAUCCUGGGAAACAGG**cuugacG | - 133 - | Necro |
| TNV-D | - 125 - | guacaagc**CGGAUCCUGGGAAACAGG**uuuaacG | - 148 - | Necro |
| RCNMV1 | - 150 - | accggcau**CGGA**c**CCUGGGAAACAGG**uaccuaG | - 259 - | Diantho |
| SCNMV1 | - | accggucu**CGGA**c**CCUGG**u**AAACAGG**uaccuaG | | Diantho |
| CRSV1 | - 136 - | cagugauc**CGGAUCCUG**a**GAAACAGG**caguccG | - 183 - | Diantho |
| Consensus: | | **CGGAUCCUGGGAAACAGGY-----G** | | |
| BamHI4837 Fill-in | | **CGGAUCCUGGGAAACAGG** (insertion: **gauc**) | | |
| STNV | - 54 - | ucuggAgc**C**acu**UCCUGGAA**g**CAG**aaauccaa (insertion: uggu) | - 530 - | Necro |

| | |
|---|---|
| PAV | SEQ ID NO. 5 |
| MAV | SEQ ID NO. 6 |
| SDV | SEQ ID NO. 7 |
| TNV-A | SEQ ID NO. 8 |
| TNV-D | SEQ ID NO. 9 |
| RCNMV1 | SEQ ID NO. 10 |
| SCNMV1 | SEQ ID NO. 11 |
| CRSV1 | SEQ ID NO. 12 |
| Consensus | SEQ ID NO. 13 |
| BamHI4837 Fill-in | SEQ ID NO. 14 |
| STNV | SEQ ID NO. 15 |

FIGURE 4

| | nt from end of 3′ ORF | | nt to end of genome | Virus Group | Accession number |
|---|---|---|---|---|---|
| PAV | - 15 - | cacaaau**CGGAUCCUGGGAAACAGG**cagaacu | - 818 - | Luteo I | XO7653 |
| MAV | - 16 - | ca.aaua**CGGAUCCUGGGAAACAGG**cagaacu | - 806 - | Luteo I | D11028 |
| SDV | - 62 - | cugucgug**GGAUCCUGGGAAACAGG**uucgguG | - 559 - | Luteo I | L24049 |
| TNV-A | - 52 - | acggaga**CGGAUCCUGGGAAACAGG**cuugacG | - 134 - | Necro | X58455 |
| TNV-D | - 126 - | uacaagc**CGGAUCCUGGGAAACAGG**uuuaacG | - 149 - | Necro | D00942 |
| RCNMV1 | - 151 - | ccggcau**CGGA**c**CCUGGGAAACAGG**uaccuaG | - 260 - | Diantho | J04357 |
| SCNMV1 | 142 - | ccggucu**CGGA**c**CCUGG**u**AAACAGG**uaccuaG | 262 | Diantho | L07884 |
| CRSV1 | - 137 - | agugauc**CGGAUCCUG**a**GAAACAGG**caguccG | - 184 - | Diantho | L18870 |
| Consensus: | | **CGGAUCCUGGGAAACAGGY-----G** | | | |
| BamHI4837 | Fill-in | **CGGAUCCUGGGAAACAGG** (**gauc**) | | | |
| STNV | - 55 - | cuggAgc**C**acu**UCCUGGAA**g**CAG**aaauccaa (uggu) | - 531 - | Necro | V01468 |

| | |
|---|---|
| BYDV-PAV | SEQ ID NO. 16 |
| BYDV-MAV | SEQ ID NO. 17 |
| SDV | SEQ ID NO. 18 |
| TNV-A | SEQ ID NO. 19 |
| TNV-D | SEQ ID NO. 20 |
| RCNMV1 | SEQ ID NO. 21 |
| SCNMV1 | SEQ ID NO. 22 |
| CRSV1 | SEQ ID NO. 23 |
| Consensus | SEQ ID NO. 24 |
| BamHI4837 Fill-in | SEQ ID NO. 25 |
| STNV | SEQ ID NO. 26 |

FIGURE 13

Wildtype 3'TE

```
                              SEQUENCE LISTING


(1) GENERAL INFORMATION:

   (iii) NUMBER OF SEQUENCES:  26


(2) INFORMATION FOR SEQ ID NO:1:

     (i) SEQUENCE CHARACTERISTICS:
          (A) LENGTH:  27 bp
          (B) TYPE:  nucleic acid
          (C) STRANDEDNESS:  single-stranded
          (D) TOPOLOGY:  linear

    (ii) MOLECULE TYPE:
          (A) DESCRIPTION:  other nucleic acid

   (iii) HYPOTHETICAL:  no

    (iv) ANTI-SENSE:  no

     (v) FRAGMENT TYPE:

    (vi) ORIGINAL SOURCE:

   (vii) IMMEDIATE SOURCE:

  (viii) POSITION IN GENOME:

    (ix) FEATURE:

     (x) PUBLICATION INFORMATION:

    (xi) SEQUENCE DESCRIPTION:SEQ ID NO:   1:

GCGGAGCTCA GACAACACCA CTAGCAC                                          27


(2) INFORMATION FOR SEQ ID NO:2:

     (i) SEQUENCE CHARACTERISTICS:
          (A) LENGTH:  28 bp
          (B) TYPE:  nucleic acid
          (C) STRANDEDNESS:  single-stranded
          (D) TOPOLOGY:  linear

    (ii) MOLECULE TYPE:
          (A) DESCRIPTION:  other nucleic acid

   (iii) HYPOTHETICAL:  no

    (iv) ANTI-SENSE:  no

     (v) FRAGMENT TYPE:

    (vi) ORIGINAL SOURCE:

   (vii) IMMEDIATE SOURCE:

  (viii) POSITION IN GENOME:

    (ix) FEATURE:

     (x) PUBLICATION INFORMATION:

    (xi) SEQUENCE DESCRIPTION:SEQ ID NO:   2:

GCGGAGCTCC ATCGGCCAAA CACAATAC                                         28
```

(2) INFORMATION FOR SEQ ID NO:3:

(i) SEQUENCE CHARACTERISTICS:
(A) LENGTH: 42 bp
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 3:

GCGGCGGCCG CTAATACGAC TCACTATAGG TATTTTTACA AC 42

(2) INFORMATION FOR SEQ ID NO:4:

(i) SEQUENCE CHARACTERISTICS:
(A) LENGTH: 20 bp
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 4:

TCGCGATCCA GACTGAATGC 20

(2) INFORMATION FOR SEQ ID NO:5:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Barley Yellow Dwarf Virus (vii) IMMEDIATE SOURCE:

(viii) POSITION IN GENOME:

(ix) FEATURE:
(D) OTHER INFORMATION: GenBank Accession No. X07653

(x) PUBLICATION INFORMATION:
(A) AUTHORS: Chaloub, B.A., et al.
(B) TITLE:
(C) JOURNAL: Archives of Virology
(D) VOLUME: 139
(E) ISSUE:
(F) PAGES: 403-416
(G) DATE:1994

(xi) SEQUENCE DESCRIPTION:SEQ ID NO: 5:

GCACAAAUCG GAUCCUGGGA AACAGGCAGA ACU 33

(2) INFORMATION FOR SEQ ID NO:6:

(i) SEQUENCE CHARACTERISTICS:
(A) LENGTH: 32
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Barley Yellow Dwarf Virus (vii) IMMEDIATE SOURCE:

(viii) POSITION IN GENOME:

(ix) FEATURE:
(D) OTHER INFORMATION: GenBank Accession No. D11028

(x) PUBLICATION INFORMATION:

(xi) SEQUENCE DESCRIPTION:SEQ ID NO: 6:

GCAAAUACGG AUCCUGGGAA ACAGGCAGAA CU 32

(2) INFORMATION FOR SEQ ID NO:7:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Soybean Dwarf Virus (vii) IMMEDIATE SOURCE:

(viii) POSITION IN GENOME:

(ix) FEATURE:
(D) OTHER INFORMATION: GenBank Accession No. L24049

(x) PUBLICATION INFORMATION:

(xi) SEQUENCE DESCRIPTION:SEQ ID NO: 7:

GCUGUCGUGG GAUCCUGGGA AACAGGUUCG GUG 33

(2) INFORMATION FOR SEQ ID NO:8:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Tobacco Necrosis Virus Strain A (vii) IMMEDIATE SOURCE:

(viii) POSITION IN GENOME:

(ix) FEATURE:
(D) OTHER INFORMATION: GenBank Accession No. X58455

(x) PUBLICATION INFORMATION:

(xi) SEQUENCE DESCRIPTION:SEQ ID NO: 8:

GACGGAGACG GAUCCUGGGA AACAGGCUUG ACG 33

(2) INFORMATION FOR SEQ ID NO:9:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Tobacco Necrosis Virus Strain D (vii) IMMEDIATE SOURCE:

(viii) POSITION IN GENOME:

(ix) FEATURE:
(D) OTHER INFORMATION: GenBank Accession No. D00942

(x) PUBLICATION INFORMATION:

(xi) SEQUENCE DESCRIPTION:SEQ ID NO: 9:

GUACAAGCCG CAUCCUGGGA AACAGGUUUA ACG 33

(2) INFORMATION FOR SEQ ID NO:10:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Red Clover Necrotic Mosaic Virus RNA1

(vii) IMMEDIATE SOURCE:

(viii) POSITION IN GENOME:

(ix) FEATURE:
(D) OTHER INFORMATION: GenBank Accession No. J04357

(x) PUBLICATION INFORMATION:

(xi) SEQUENCE DESCRIPTION:SEQ ID NO: 10:

ACCGGCAUCG GACCCUGGGA AACAGGUACC UAG 33

(2) INFORMATION FOR SEQ ID NO:11:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Sweet Clover Necrotic Mosaic Virus RNA1

(vii) IMMEDIATE SOURCE:

(viii) POSITION IN GENOME:

(ix) FEATURE:
(D) OTHER INFORMATION: GenBank Accession No. L07884

(x) PUBLICATION INFORMATION:

(xi) SEQUENCE DESCRIPTION:SEQ ID NO: 11:

ACCGGUCUCG GACCCUGGUA AACAGGUACC UAG 33

(2) INFORMATION FOR SEQ ID NO:12:

(i) SEQUENCE CHARACTERISTICS:
(A) LENGTH: 33
(B) TYPE: nucleic acid
(C) STRANDEDNESS: single-stranded
(D) TOPOLOGY: linear (ii) MOLECULE TYPE:

(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Carnation Ringspot Virus RNA1

(vii) IMMEDIATE SOURCE:

(viii) POSITION IN GENOME:

(ix) FEATURE:
(D) OTHER INFORMATION: GenBank Accession No. L18870

(x) PUBLICATION INFORMATION:

(xi) SEQUENCE DESCRIPTION:SEQ ID NO: 12:

CAGUGAUCCG GAUCCUGAGA AACAGGCAGU CCG 33

(2) INFORMATION FOR SEQ ID NO:13:

(i) SEQUENCE CHARACTERISTICS:
(A) LENGTH: 20
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 13:

CGGAUCCUGG GAAACAGGYG 20

(2) INFORMATION FOR SEQ ID NO:14:

(i) SEQUENCE CHARACTERISTICS:
(A) LENGTH: 22
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

-continued (ix) FEATURE:

(x) PUBLICATION INFORMATION:

(xi) SEQUENCE DESCRIPTION:SEQ ID NO: 14:

CGGAUCGAUC CUGGGAAACA GG 22

(2) INFORMATION FOR SEQ ID NO:15:

(i) SEQUENCE CHARACTERISTICS:
(A) LENGTH: 36
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Satellite Tobacco Necrosis Virus (vii) IMMEDIATE SOURCE:

(viii) POSITION IN GENOME:

(ix) FEATURE:
(D) OTHER INFORMATION: GenBank Accession No. V01468

(x) PUBLICATION INFORMATION:

(xi) SEQUENCE DESCRIPTION:SEQ ID NO: 15:

UCUGGAGCCA CUUCCUGGUG GUAAGCAGAA AUCCAA 36

(2) INFORMATION FOR SEQ ID NO:16:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Barley Yellow Dwarf Virus (vii) IMMEDIATE SOURCE:

(viii) POSITION IN GENOME:

(ix) FEATURE:
(D) OTHER INFORMATION: Gene Bank Accession No. X07653

(x) PUBLICATION INFORMATION:

(xi) SEQUENCE DESCRIPTION:SEQ ID NO: 16:

CACAAAUCGG AUCCUGGGAA ACAGGCAGAA C 31

(2) INFORMATION FOR SEQ ID NO:17:

(i) SEQUENCE CHARACTERISTICS:

-continued (A) LENGTH: 30
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Barley Yellow Dwarf Virus (vii) IMMEDIATE SOURCE:

(viii) POSITION IN GENOME:

(ix) FEATURE:
(D) OTHER INFORMATION: GenBank Accession No. D11028

(x) PUBLICATION INFORMATION:

(xi) SEQUENCE DESCRIPTION:SEQ ID NO: 17:

CAAAUACGGA UCCUGGGAAA CAGGCAGAAC 30

(2) INFORMATION FOR SEQ ID NO:18:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Soybean Dwarf Virus (vii) IMMEDIATE SOURCE:

(viii) POSITION IN GENOME:

(ix) FEATURE:
(D) OTHER INFORMATION: GenBank Accession No. L24049

(x) PUBLICATION INFORMATION:

(xi) SEQUENCE DESCRIPTION:SEQ ID NO: 18:

CUGUCGUGGG AUCCUGGGAA ACAGGUUCGG U 31

(2) INFORMATION FOR SEQ ID NO:19:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Tobacco Necrosis Virus Strain A (vii) IMMEDIATE SOURCE:

(viii) POSITION IN GENOME:

(ix) FEATURE:
(D) OTHER INFORMATION: GenBank Accession No. X58455

(x) PUBLICATION INFORMATION:

(xi) SEQUENCE DESCRIPTION:SEQ ID NO: 19:

ACGGAGACGG AUCCUGGGAA ACAGGCUUGA C 31

(2) INFORMATION FOR SEQ ID NO:20:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Tobacco Necrosis Virus Strain D (vii) IMMEDIATE SOURCE:

(viii) POSITION IN GENOME:

(ix) FEATURE:
(D) OTHER INFORMATION: GenBank Accession No. D00942

(x) PUBLICATION INFORMATION:

(xi) SEQUENCE DESCRIPTION:SEQ ID NO: 20:

UACAAGCCGC AUCCUGGGAA ACAGGUUUAA C 31

(2) INFORMATION FOR SEQ ID NO:21:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Red Clover Necrotis Mosaic Virus RNA1

(vii) IMMEDIATE SOURCE:

(viii) POSITION IN GENOME:

(ix) FEATURE:
(D) OTHER INFORMATION: GenBank Accession No. J04357

(x) PUBLICATION INFORMATION:

(xi) SEQUENCE DESCRIPTION:SEQ ID NO: 21:

CCGGCAUCGG ACCCUGGGAA ACAGGUACCU A 31

(2) INFORMATION FOR SEQ ID NO:22:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Sweet Clover Necrotic Mosaic Virus RNA1

(vii) IMMEDIATE SOURCE:

(viii) POSITION IN GENOME:

(ix) FEATURE:
(D) OTHER INFORMATION: GenBank Accession No. L07884

(x) PUBLICATION INFORMATION:

(xi) SEQUENCE DESCRIPTION:SEQ ID NO: 22:

CCGGUCUCGG ACCCUGGUAA ACAGGUACCU A 31

(2) INFORMATION FOR SEQ ID NO:23:

(i) SEQUENCE CHARACTERISTICS:
(A) LENGTH: 31
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Carnation Ringspot Virus RNA1

(vii) IMMEDIATE SOURCE:

(viii) POSITION IN GENOME:

(ix) FEATURE:
(D) OTHER INFORMATION: GenBank Accession No. L18870

(x) PUBLICATION INFORMATION:

(xi) SEQUENCE DESCRIPTION:SEQ ID NO: 23:

AGUGAUCCGG AUCCUGAGAA ACAGGCAGUC C 31

(2) INFORMATION FOR SEQ ID NO:24:

(i) SEQUENCE CHARACTERISTICS:
(A) LENGTH: 19
(B) TYPE: nucleic acid (C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 24:

CGGAUCCUGG GAAACAGGY 19

(2) INFORMATION FOR SEQ ID NO:25:

(i) SEQUENCE CHARACTERISTICS:
(A) LENGTH: 23
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 25:

CGGAUCGAUC CUGGGAAACA GGY 23

(2) INFORMATION FOR SEQ ID NO:26:

(i) SEQUENCE CHARACTERISTICS:
(A) LENGTH: 34
(B) TYPE: nucleic acid
(C) STRANDEDNESS: single-stranded
(D) TOPOLOGY: linear (ii) MOLECULE TYPE:
(A) DESCRIPTION: genomic RNA (iii) HYPOTHETICAL: no (iv) ANTI-SENSE: no (v) FRAGMENT TYPE:

(vi) ORIGINAL SOURCE:
(A) ORGANISM: Satellite Necrosis Virus (vii) IMMEDIATE SOURCE:

-continued (viii) POSITION IN GENOME:

(ix) FEATURE:
(D) OTHER INFORMATION: GenBank Accession No. V01468

(x) PUBLICATION INFORMATION:

(xi) SEQUENCE DESCRIPTION:SEQ ID NO: 26:

```
CUGGAGCCAC UUCCUGGUGG UAAGCAGAAA UCCA                    34
```

CAP-INDEPENDENT TRANSLATION SEQUENCES DERIVED FROM BARLEY YELLOW DWARF VIRUS

CROSS REFERENCE TO PRIOR APPLICATION

This application claims benefit of priority of U.S. provisional application 60/017,199 filed on May 20, 1996.

FEDERAL FUNDING LEGEND

This invention was created in part using funds from the federal government under National Research Initiative Grant No. 9137036424 and USDA Grant No. 9137036424. The United States government, therefore, has certain rights in this invention.

BACKGROUND OF THE INVENTION

1. Field of the Invention

The present invention relates generally to the fields of plant biotechnology and molecular genetics of eucaryotic gene expression and translation. More specifically, the present invention relates to novel cap-independent translation sequences derived from barley yellow dwarf virus.

2. Description of the Related Art

Translation is the step in gene expression at which proteins are synthesized. The genetic code is decoded from a messenger RNA (mRNA) sequence to protein sequence. All genes that encode proteins must be translated. mRNAs of eukaryotes (plants, animals and fungi) are transcribed (synthesis of mRNA from DNA) by RNA polymerase II. All polymerase II transcripts, except histone genes, are modified post-transcriptionally to contain a $m^7G$ cap structure at the 5' end (beginning) and a polyadenylate tract (poly(A) tail) at the 3' end (end). These modifications are required for translation of the mRNA.

Models for translation initiation in eukaryotes call for ribosome recognition of the 5' cap of mRNA, mediated by initiation factors, followed by 5' to 3' scanning until the first AUG is reached at which protein synthesis ensues[1,2]. However, the 3' untranslated region communicates with the 5' end of an mRNA in regulating initiation of translation. Cis-acting signals in the 3' untranslated regions of certain mRNAs can be recognized by specific regulatory proteins that inhibit translation initiation[3]. Poly(A) tails[4,5] or functionally equivalent domains in some plant viruses[6], stimulate initiation of translation. The 5' cap and poly(A) tail act synergistically to stimulate initiation in vivo[5] but cannot substitute for each other. The 5' cap strongly stimulates initiation in reticulocyte lysates and wheat germ, but stimulation by poly(A) is minimal in either system[5,7]. In addition to stimulating translation initiation, both components confer mRNA stability in vivo[8].

Sequences in the 5' UTRs of some viral RNAs can substitute for a cap[9-11]. For example, the Internal Ribosome Entry Site (IRES) of picornaviruses[10,12] facilitates 40S ribosomal subunit binding far from the 5' end of the mRNA (which lacks a cap) in the absence of translation factors (eIF-4F) that are necessary for cap-dependent translation initiation. Like the 5' cap, these sequences are located 5' of the AUG codon at which protein synthesis begins.

A sequence (3' translation enhancer, 3'TE) located between bases 4513 and 5009 of the 5677 nucleotide genomic RNA of barley yellow dwarf virus, PAV serotype (PAV) facilitates efficient translation when located in the 3' untranslated regions of uncapped viral or heterologous mRNAs in wheat germ translation extracts (WGE)[13]. These constructs also contained the viral 5' untranslated region. A similar phenomenon has been observed with the 1200 nucleotide satellite tobacco necrosis virus (STNV) RNA in wheat germ translation extracts [14,15]. In none of these cases has the 3' untranslated region been shown to function in vivo.

Sequences in the 5'UTR and 3'UTR of satellite tobacco necrosis virus also confer efficient translation on uncapped mRNAs in wheat germ translation extracts (Danthinne et al., 1993; Timmer et al., 1993). The 5'UTR of tobacco etch virus (TEV) confers efficient translation of uncapped mRNAs in vitro and in vivo and translation is stimulated a further 15-fold in plant cells when the mRNA containing the tobacco etch virus 5'UTR is capped (Carrington and Freed, 1990). The 5'UTRs of alfalfa mosaic virus (AIMV) and tobacco mosaic virus (Ω sequence of tobacco mosaic virus) confer efficient translation of capped mRNAs (Sleat and Wilson, 1992). Both are used in vectors for high level gene expression in transgenic plants. The barley yellow dwarf virus-PAV translation enhancing sequences show no apparent sequence similarity to any of the above sequences.

The satellite tobacco necrosis virus and tobacco etch virus sequences do not seem to confer as much stimulation of translation of uncapped RNAs in vitro. The activity of satellite tobacco necrosis virus sequences in cells or plants is unknown. The alfalfa mosaic virus and tobacco mosaic virus sequences differ from the barley yellow dwarf virus-PAV sequences in that they do not confer efficient translation of uncapped mRNAs in vivo. The tobacco etch virus sequence does not fully substitute for the presence of a 5' cap.

Almost all eukaryotic cellular mRNAs contain a 5' $m^7G$ (5')ppp(5')N cap structure that is required for efficient initiation of translation. According to the ribosome scanning model of eukaryotic translation initiation, initiation factor eIF4F specifically recognizes the 5' cap structure and, with other initiation factors such as eIF3, recruits the 43S ribosomal subunit initiation complex that then scans 5' to 3' along the mRNA. When the first (or second in the case of leaky scanning) AUG codon is reached, the 60S ribosomal subunit joins and peptide elongation ensues.

Although the ribosome scanning model explains the mechanisms of various translational regulatory elements in the 5' UTRs of mRNAs, numerous examples exist of translational control elements in the 3'UTRs of mRNAs. The 3' poly(A) tail, found on most eukaryotic cellular mRNAs, stimulates translation initiation and stabilizes mRNA. The 5' cap and poly(A) tail act synergistically to stimulate initiation in vivo and in a yeast in vitro translation system. Viral RNAs that lack a poly(A) tail, sequences in the 3'UTR, such as the pseudoknot-rich domain of tobacco mosaic virus (TMV) appear to functionally substitute for a poly(A) tail to stimulate translation in conjunction with the 5' cap. Other cis-acting elements in 3' UTRs control translation initiation either by modulating poly(A) tail length during embryo development, or via binding of a specific regulatory protein that inhibits initiation. In all these examples, the mRNA must have a 5' cap for the 3' element to function. Thus, in previously described mRNAs, cap recognition is likely an essential component in the communication between 3' and 5' ends.

Mammalian eIF4F complex is comprised of eIF4E (the cap-binding subunit), eIF4G (p220), and the loosely-associated eIF4A (helicase). Plant cells contain two forms of the 4F complex: eIF4F, consisting of 26 kDa and 220 kDa subunits (homologous to eIF4E and eIF4G, respectively), and eIFiso4F, consisting of 28 kDa and 86 kDa subunits.

eIF4A probably has the same function in plants but does not co-purify with eIF4F, so it is not considered a subunit of this complex. In defined cell-free systems, capped mRNAs have a reduced requirement for eIF4F compared to uncapped mRNAs.

Many viral mRNAs lack a 5' cap or a poly(A) tail, or both. They have evolved ways of ensuring efficient translation of their genes from uncapped mRNAs, often at the expense of the host cell. The most well-documented example is the translation of picornavirus RNAs. Picornaviral RNAs lack a 5' cap structure and have an extremely long, highly structured 5' untranslated region, including many AUG codons upstream of the start codon of the main open reading frame. Rather than scanning from the 5' end, ribosomes bind internally in this long leader at the internal ribosomal entry site just upstream of the start codon, in a cap-independent manner. Although IRES-mediated cap-independent translation does not comform to the rule of 5' cap-eIF4E recognition, it still employs the other canonical initiation factors including the eIF4G subunit of eIF4F, and follows the scanning concept of ribosome binding the 5' UTR followed by scanning in a 3' direction until the appropriate start codon is reached for initiation of translation.

The prior art is deficient in the lack of effective means of stimulating high level expression of proteins from uncapped mRNAs in vivo. The present invention fulfills this long-standing need and desire in the art.

SUMMARY OF THE INVENTION

For efficient initiation of translation by the ribosome, eukaryotic messenger RNAs normally contain a 5' cap structure (usually $m^7G(5')ppp(5')N$). At the 3' ends of mRNAs, a polyadenylate tract stimulates translation initiation in conjunction with the 5' cap, but does not substitute for the cap. The present invention demonstrates that a plant viral sequence located in the 3' untranslated region (UTR) which, in conjunction with the 5' untranslated region, functionally substitutes for a 5' cap structure. It stimulates translation of a reporter gene from uncapped mRNA by 30 to 100-fold in vitro and in vivo. A four base duplication destroyed the stimulatory activity. Translatability was recovered by addition of a 5' cap to this mRNA. The sequence is required for viral RNA replication. The present invention represents a new kind of translation stimulatory element that requires re-evaluation of the mechanism by which the 5' cap facilitates translation. This sequence useful for high level expression of proteins from uncapped mRNAs.

In one embodiment of the present invention, there is provided a method of increasing the production of a protein translated from an uncapped eukaryotic messenger ribonucleic acid (mRNA), comprising the steps of: selecting a nucleotide sequence encoding a protein to be expressed; joining nucleotides 1–168 of the barley yellow dwarf virus RNA, PAV serotype to the 5' untranslated region of said uncapped mRNA, said nucleotides 1–168 comprising the 5' untranslated region plus first 27 nucleotides of the open reading frame of the barley yellow dwarf virus RNA; linking nucleotides 4513–5677 of the barley yellow dwarf virus RNA, PAV serotype, to the 3' untranslated region of said uncapped mRNA; and expressing the protein.

In another embodiment of the present invention, there is provided a DNA molecule which comprises: (a) a promoter region which functions in plant cells to cause the production of an RNA sequence, which is operably linked to (b) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA; (c) a coding sequence, wherein said coding sequence is heterologous to said 5' untranslated region, which is operably linked to (d) a 3' untranslated region that functions in plant cells to cause the termination of transcription, said 3' untranslated region comprising nucleotides 4513–5677 of the barley yellow dwarf virus RNA.

In yet another embodiment of the present invention, there is provided a method for providing enhanced gene expression in plants which comprises: (a) transforming plant cells with a DNA molecule which comprises: (i) a promoter region which functions in plant cells to cause the production of an RNA sequence, which is operably linked to (ii) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA; (iii) a coding sequence containing a coding region), wherein said coding sequence is heterologous to said 5' untranslated region, which is operably linked to (iv) a 3' untranslated region that functions in plant cells to cause the termination of transcription, said 3' untranslated region comprising nucleotides 4513–5677 of the barley yellow dwarf virus RNA; (b) selecting said plant cells which have been transformed; (c) regenerating said plant cells to provide a differentiated plant; and (d) selecting a transformed plant which expresses said gene.

In yet another embodiment of the present invention, there is provided a method of increasing the production of a protein translated from an uncapped eukaryotic messenger ribonucleic acid (mRNA), comprising the steps of: selecting a nucleotide sequence encoding a protein to be expressed; joining nucleotides 4817–4925 of the barley yellow dwarf virus RNA, PAV serotype to the 5' untranslated region of said uncapped mRNA; and expressing the protein.

In yet another embodiment of the present invention, there is provided a DNA molecule which comprises: (a) a promoter region which functions in plant cells to cause the production of an RNA sequence, which is operably linked to (b) a 5' untranslated region including a 5' translation enhancing segment, said 5' translation enhancing segment comprising nucleotides 4817–4925 of the barley yellow dwarf virus RNA, PAV serotype; (c) a coding sequence, wherein said coding sequence is heterologous to said 5' untranslated region, which is operably linked to (d) a 3' untranslated region that functions in plant cells to cause the termination of transcription.

In yet another embodiment of the present invention, there is provided a method for providing enhanced gene expression which comprises: (a) transforming cells with a DNA molecule which comprises: (i) a promoter region which functions in said cells to cause the production of an RNA sequence, which is operably linked to (ii) a 5' untranslated region including a 5' translation enhancing segment, said 5' translation enhancing segment comprising nucleotides 4817–4925 of the barley yellow dwarf virus RNA, PAV serotype; (iii) a coding sequence, wherein said coding sequence is heterologous to said 5' untranslated region, which is operably linked to (iv) a 3' untranslated region that functions in said cells to cause the termination of transcription; (b) selecting said cells which have been transformed; (c) regenerating said cells to provide a differentiated plant; and (d) selecting a transformed host which expresses said gene.

The present invention also discloses that the 3' translation enhancer (3'TE) confers cap-independent translation in yeast spheroplasts. The 3'TE also functions in an in vitro translation system derived from yeast that is poly(A) tail-dependent and accurately represents the in vivo situation, in terms of the effects of 5' cap and poly(A) tail. The 3'TE could also be used with a poly(A) tail in yeast to boost expression further. Using this or other optimization enhancers, one may use the sequence in eukaryotes generally (plants, animals and fungi).

The 5' end of the 3'TE sequence needed for full activity in vivo is shown to be between bases bases 4513 and 4817. The 3'TE works with other reporter genes besides GUS, e.g., the same stimulation by the 3'TE and 5'UTR is observed when the coding region is replaced with the luciferase (LUC) reporter gene. The 5' UTR of BYDV-PAV subgenomic RNA1 (bases 2670–2858) also functions in conjuction with the 3'TE despite having little sequence similarity to the 5'UTR of genomic RNA. The 5' extremity of the 5'UTR in genomic RNA that is needed for 3'TE activity is base 56, i.e., the first 55 bases of the genomic 5'UTR can be deleted without affecting 3'TE function.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1B shows the wheat germ translation of indicated transcripts. 0.2 pmol of each mRNA was translated and their products analysed electrophoretically as in Wang, S., et al., *J. Biol. Chem.,* 270:13446–13452, (1995). Molecular weights (in kDa) of translation products of brome mosaic virus (BMV) RNA (lane 1) (99 and 104 kDa) and *E. coli uidA* (68 kDa) are at left.

The relative radioactivity in the *E. coli uidA* product was determined with a Phosphorimager is indicated below each lane. Lanes 1–5 and 6–15 represent separate experiments with lanes 5 and 8 defined as 100%. Templates used in lanes 2–5 were prepared by run-off transcription from plasmids linearized with the indicated restriction enzymes. All transcripts in lanes 6–15 were from *Eco*RI-cut plasmids. Lanes 2–5 used uncapped transcripts. Lanes 6–15: C, capped transcript; U, uncapped transcript.

Figure 1A:
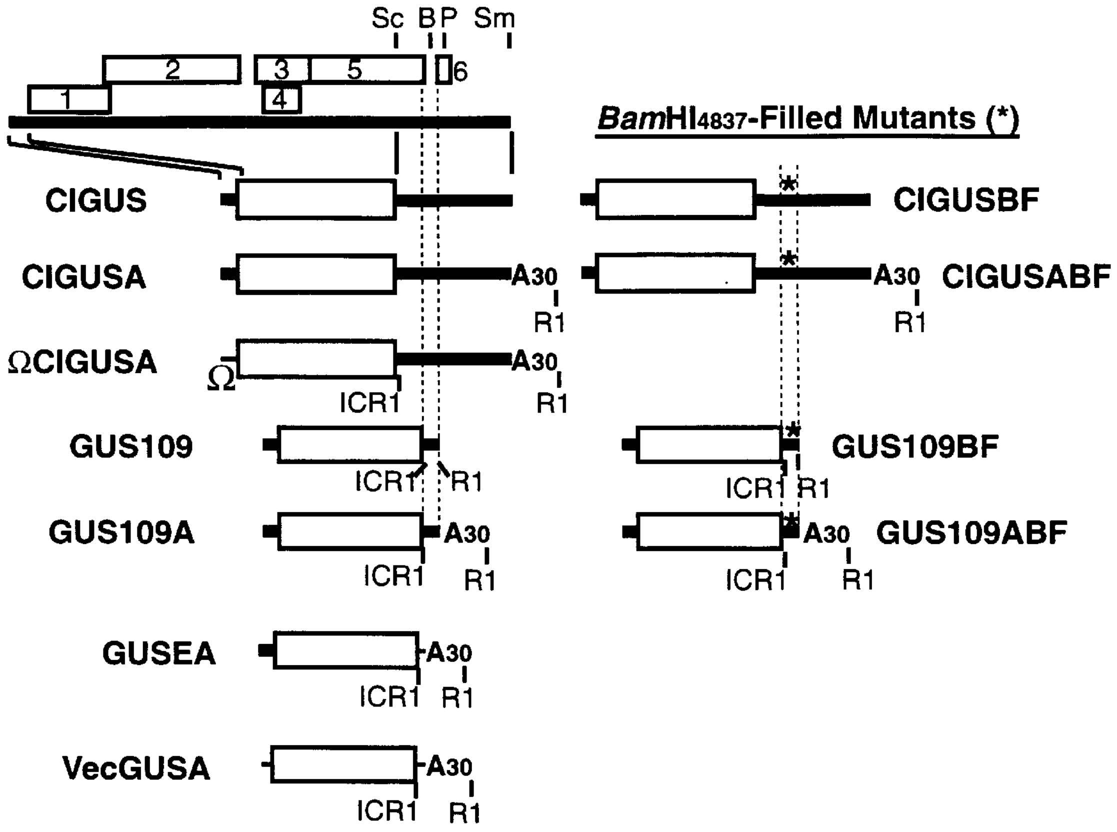
FIGS. 1A and 1B show maps of transcripts used herein. Genome organization with numbered open reading frames of PAV RNA[24] is shown at top. Abbreviations: Sc, $ScaI_{4513}$; B, $BamHI_{4837}$; P, $PstI_{5009}$; Sm, $SmaI_{5677}$ (numbered as in Miller, W., et al., *Nucleic Acids Res.,* 16:6097–6111, (1988)) R1, *Eco*RI; ICR1, *Eco*ICRI. Maps below genome map show *E. coli uidA* (open box)-encoding transcripts containing viral sequence (bold lines), vector sequence (thin lines), tobacco mosaic virus Ω (Ω), or poly(A) tails ($A_{30}$) in their untranslated regions. Maps on the right differ only by the GATC duplication at the $BamHI_{4837}$ site (*).
Figure 1B:
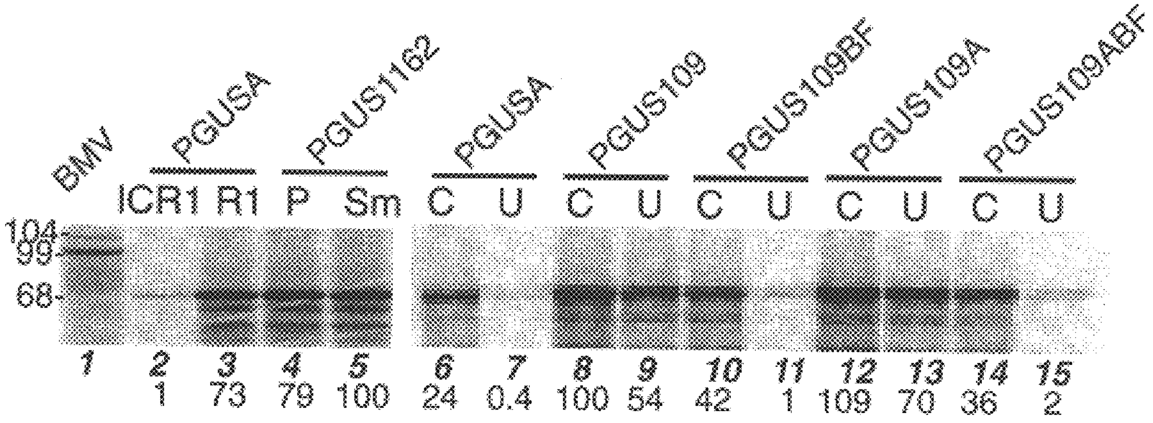
Figure 2A:
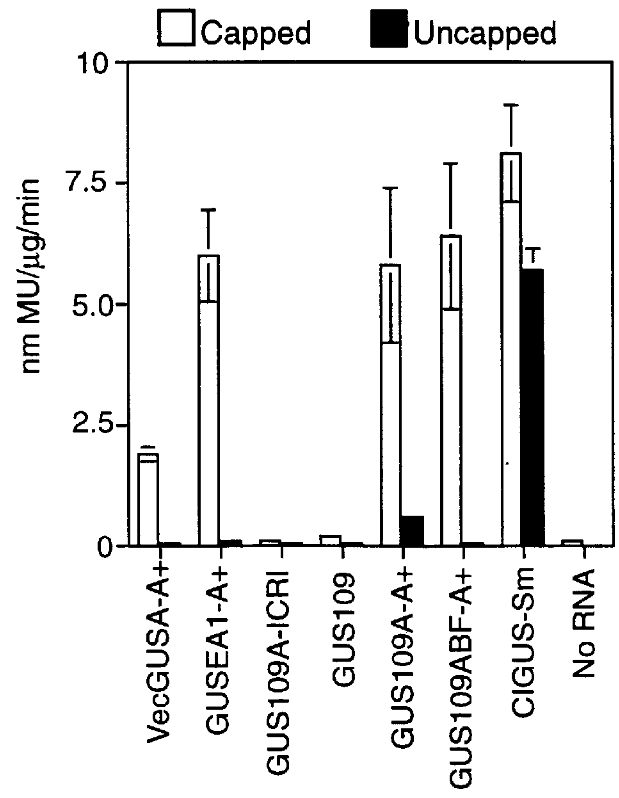
Figure 2B:
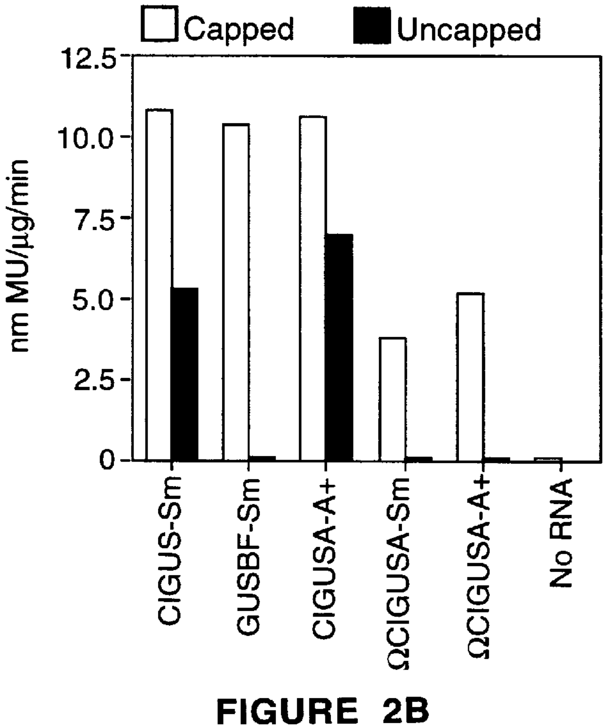
Figure 2C:
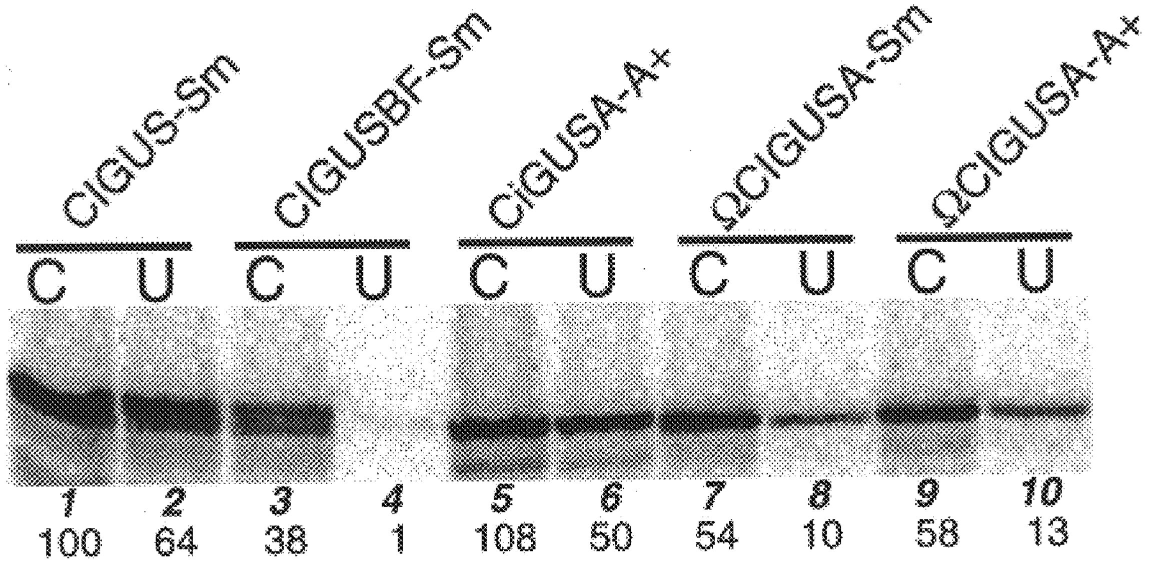

FIGS. 2A–2C show the *E. coli uidA* expression in protoplasts electroporated with transcripts, shown in FIG. 1A, containing various 5' and 3' untranslated regions. Letters following hyphens indicated restriction enzymes (abbreviated as in FIG. 1A) used to linearize plasmids prior to transcription. Transcripts containing a poly(A) tail are from EcoRI-linearized plasmids labeled A+, those from plasmids linearized with SmaI (–Sm) contain the 1163 nucleotide PAV 3'-untranslated region. FIG. 2A shows data representing averages (+/– SD) from three separate experiments each of which was performed in duplicate. FIG. 2B shows the averages from two separate experiments each of which was performed in duplicate. FIG. 2C shows the wheat germ translation products of indicated transcripts, performed as in FIG. 1.

Figure 3A:
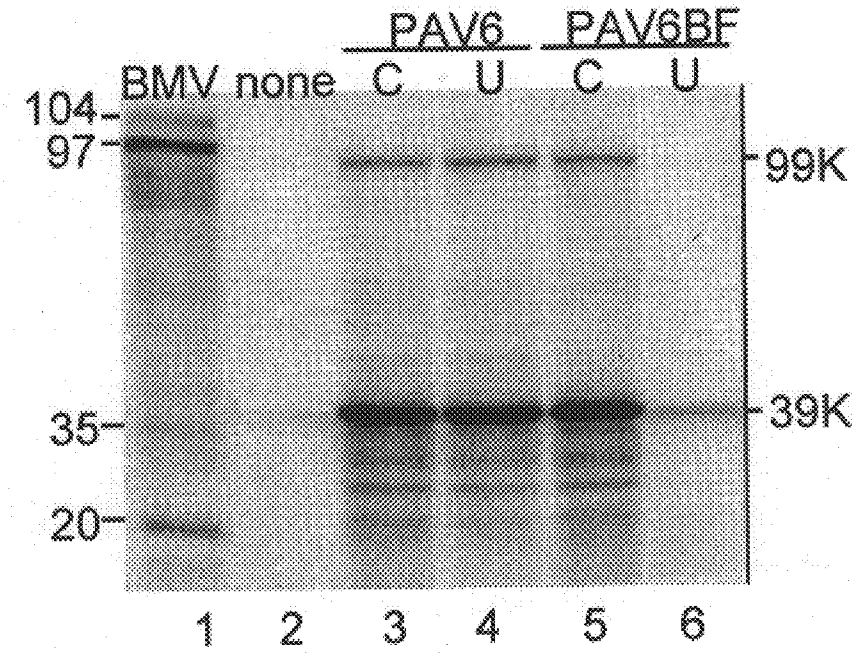
Figure 3B:
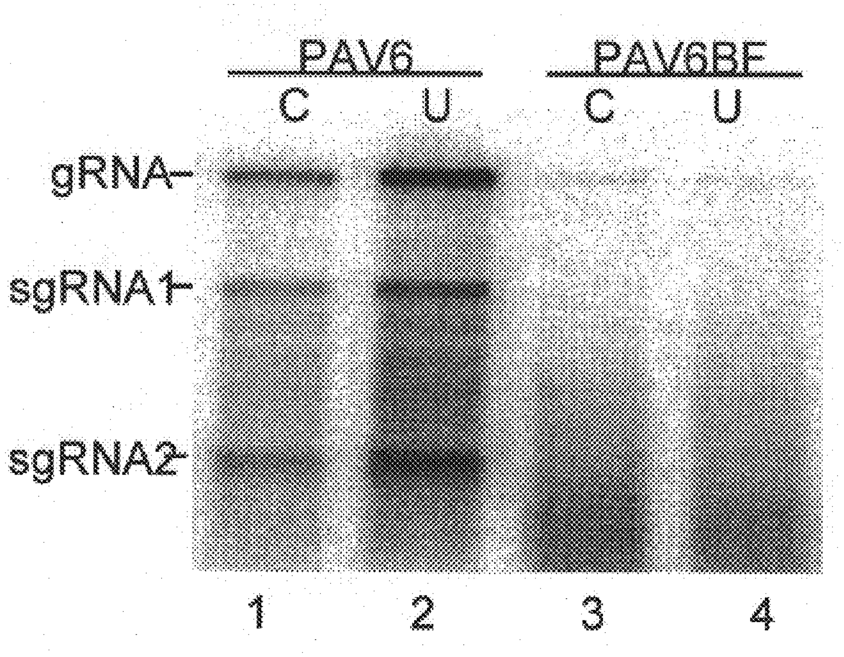

FIGS. 3A and 3B show the translation and replication of full-length PAV transcripts. C, capped; U, uncapped transcripts. FIG. 3A shows that full-length infectious transcript (PAV6[28]) and a transcript differing only by the presence of the GAUC duplication at the BamHI4837 site (PAV6BF) were translated, and the products analysed as in FIG. 1B. Mobilities of BMV markers are at left, mobilities of products of PAV ORF1 (39K) and the frameshift fusion of open reading frames 1 and 2 (99K) are indicated at right. Anomalously slow migration of 39K product has been shown previously[28]. FIG. 3B shows a northern hybridization of total RNA from oat protoplasts 48 hours after inoculation with indicated transcripts. Mobilities of PAV genomic (g) and subgenomic RNAs 1 (sg1) and 2 (sg2) are indicated. Protoplasts were prepared, inoculated and RNA analyzed by Northern hybridization as described previously[29] using a 3'-complementary probe. RNA (5–10 $\mu$g) was separated by electrophoresis on denaturing 1% agarose gels, blotted onto nylon membrane (Gene Screen, DuPont) in 25 mM phosphate buffer, and fixed by UV crosslinking. Membranes were prehybridized at 65° C. for at least 3 hours in 50% formamide, 5 X SSC, 20 mM sodium phosphate (pH 6.5), 1% SDS, and 0.2 mg/ml polyanetholesulfonic buffer containing 500,000 cpm/ml of $^{32}$P-labeled RNA transcripts for 12–16 hours at 65° C. Following hybridization, membranes were washed twice with 2 X SSC/0.1% SDS for 3 minutes each at room temperature and then washed once with 0.1X SSC/0.1% SDS for 20 minutes at 65° C. Blots were dried and exposed to X-ray film with an intensifying screen at –80° C. Blots were probed with transcript from pSP10, complementary to the 3' terminal 1450 bases of the PAV genome.

FIG. 4 shows the alignments of portions of 3' untranslated regions of indicated viral genomes. Abbreviations and Gene bank accession numbers: PAV, (X07653 and ref. 30); MAV, MAV serotype of barley yellow dwarf virus (D11028 D01213); SDV, soybean dwarf virus (L24049); TNV-A and -D, tobacco necrosis virus strains A (X58455 M33002) and D (D00942); RCNMV1, red clover necrotic mosaic virus RNA1 (J04357 M24621); SCNMV1, sweet clover necrotic mosaic virus RNA1 (L07884); CRSV1, carnation ringspot virus RNA1 (L18870); (STNV) satellite tobacco necrosis virus (V01468 J02399 M10388).

Figure 5:
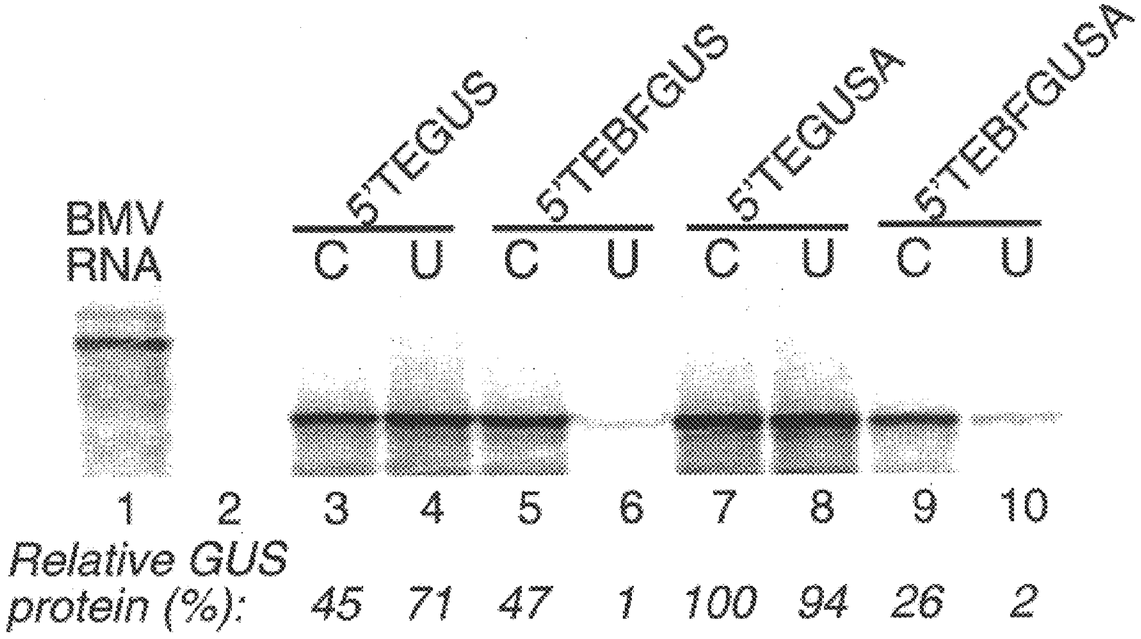

FIG. 5 shows the in vitro translation in wheat germ extract of 5' TE GUS, 5' TE BFGUS, 5' TE GUSA and 5' TE BFGUSA. Methodology was as previously described. Number refer to relative amount of GUS rpotein produced by translation. Clone: lane 3 and 4: wildtype 109 TE as 5'UTR of GUS gene; lane 5 and 6: BamHI mutant (4 base or GAUC duplication) of TE as 5'UTR of GUS gene; lanes 7 and 8: the same as 3 and 4 except polyadenylated; and lanes 9 and 10: the same as 5 and 6 except polyadenylated; lanes 1 and control represent controls with and without BMV. C refers to capped; U refers to uncapped mRNA.

Figure 6:
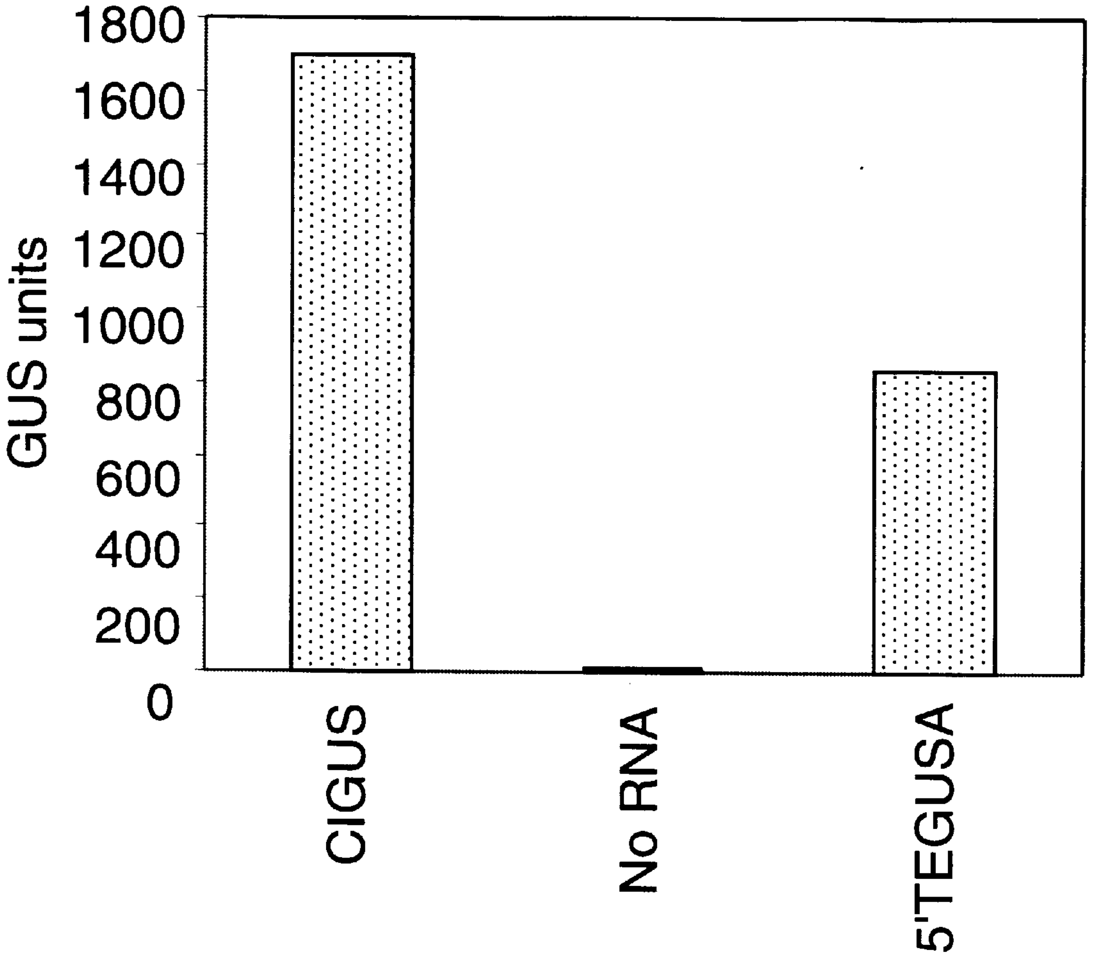

FIG. 6 shows the expression in electroporated protoplasts 24 hours after electroporation with uncapped mRNAs. For the p5'TEGUSA, the 3'TE was in the 5'UTR; no other viral sequence was present. However, the 3' poly (A) tail was present.

Figure 7A:
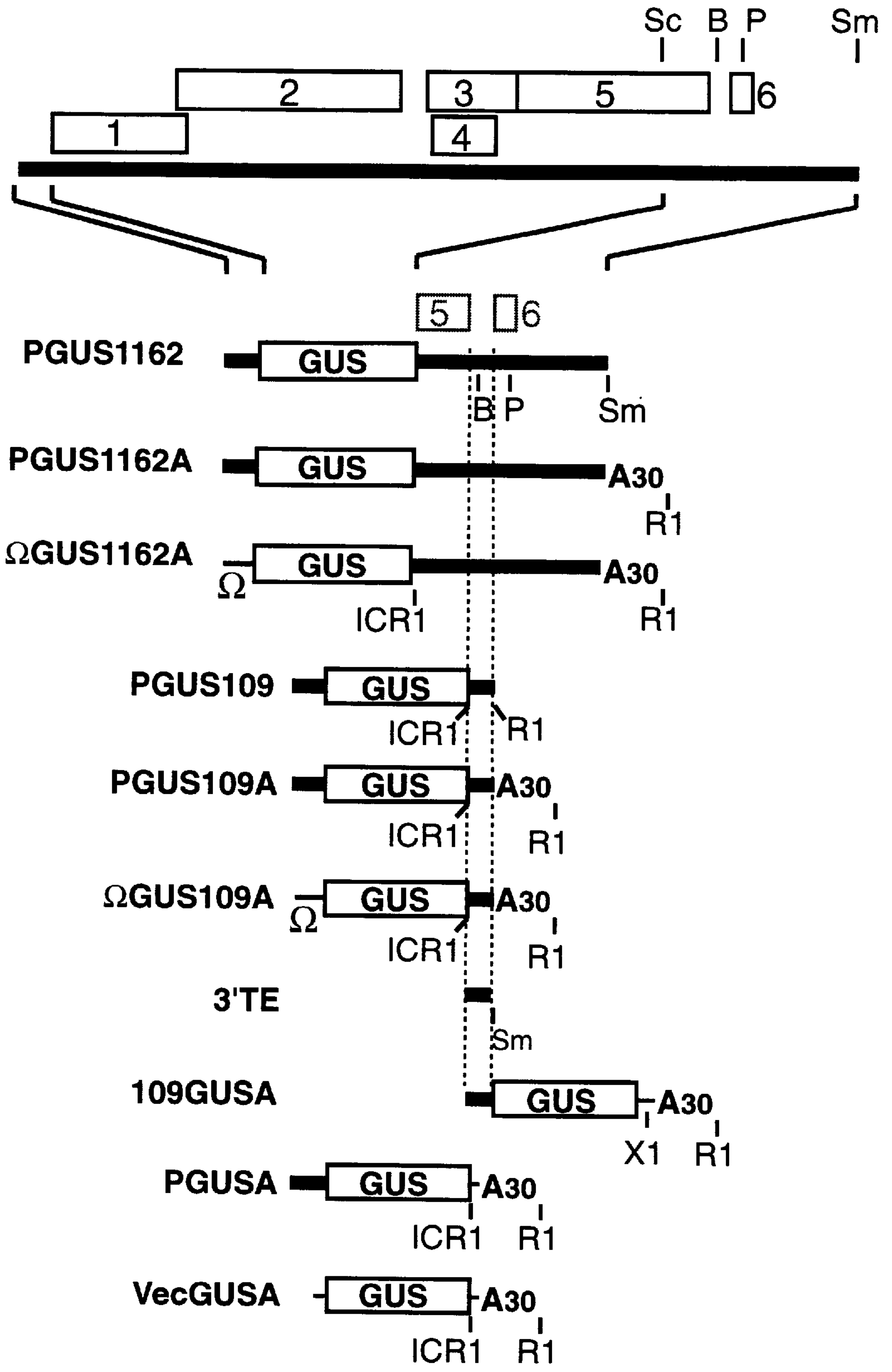
Figure 7C:
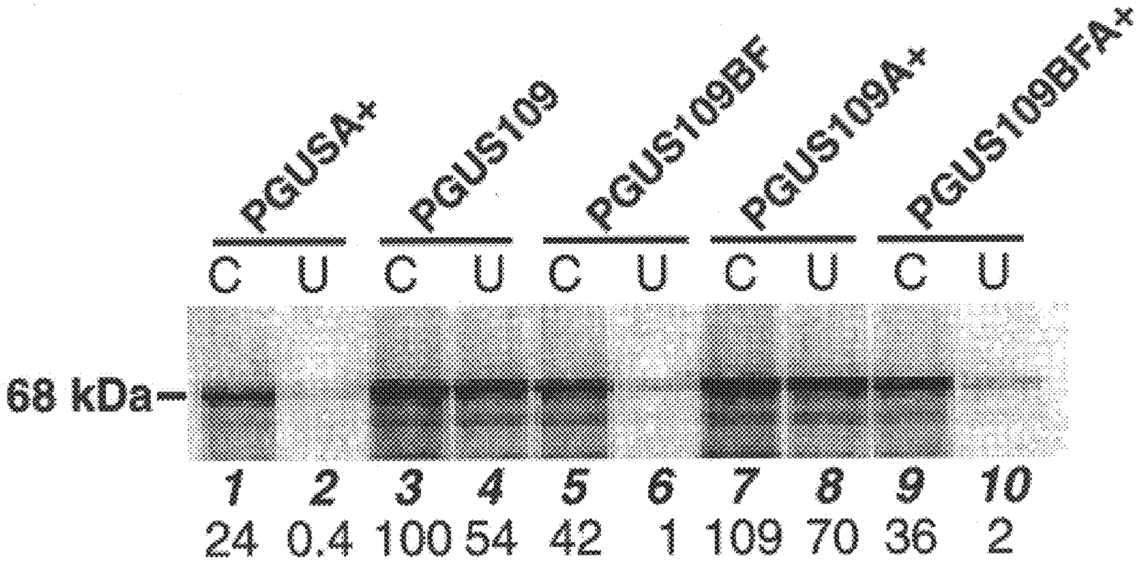
Figure 7B:
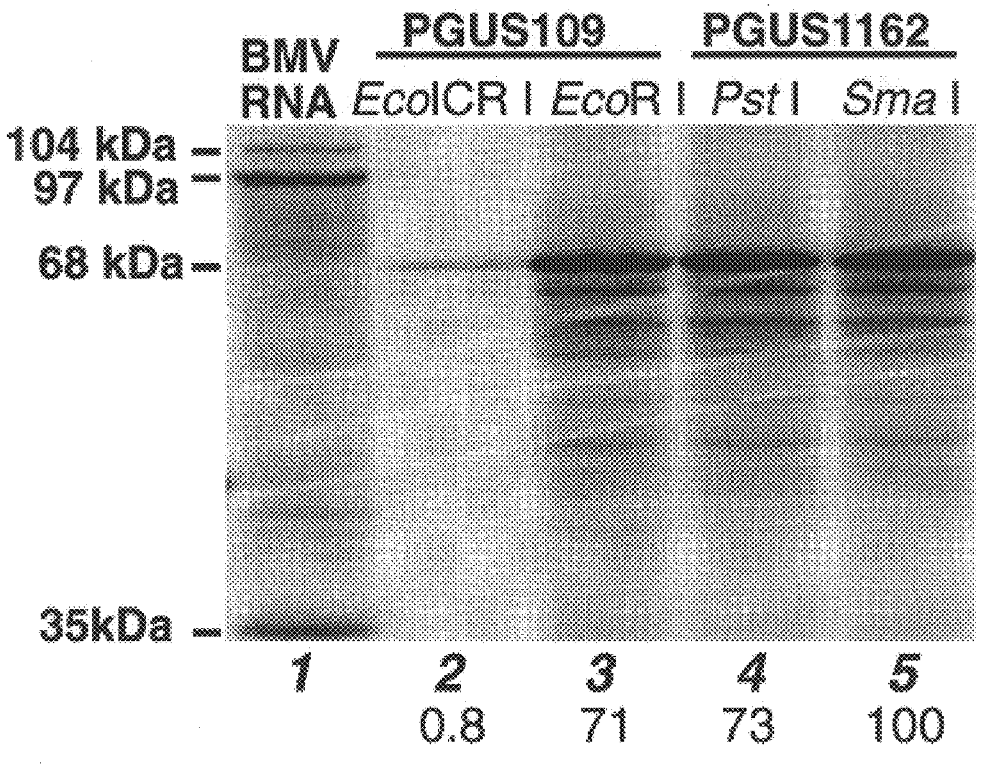

FIGS. 7A–7C show maps of transcripts. The genome organization of BYDV-PAV RNA with numbered ORFs is shown at top. Bold black line beneath ORFs (numbered boxes) indicates the 5,677 nt genomic RNA. Maps below the genome depict transcripts coding for GUS (ORF not to scale) containing viral sequence (bold lines), vector or (sequence (thin lines), or poly(A) tails ($A_{30}$) in their UTRs. The 109 nt 3'TE is the intergenic region (between dashed lines) between ORFs 5 and 6. BF transcripts are identical to those shown, except that they contain the four base duplication at the filled and re-ligated BamHI site (B) within the 109 nt 3'TE. Abbreviations: Sc, $ScaI_{4513}$; B, $BamHI_{4837}$; P, $PstI_{5009}$; Sm, $SmaI_{5677}$ (numbered as in R1, EcoRI; ICRI, EcoICRI; X1, XbaI. FIGS. 7B and 7C show wheat germ translation products of indicated transcripts. 0.2 pmol of each uncapped mRNA was translated and their products analysed electrophoretically. The relative radioactivity in the GUS product, as determined with a Phosphorimager, is indicated below each lane. FIG. 7B shows molecular weights (in kDa) of translation products of brome mosaic virus (BMV) RNA (lane 1) and GUS (68 kDa) are at left. Translation efficiency in lane 5 was defined arbitrarily as 100%. Templates used in lanes 2–5 were uncapped RNAs prepared by run-off transcription from plasmids linearized with the indicated restriction enzymes. FIGS. 7C shows that all transcripts were from EcoRI-cut plasmids, except for lanes 1 and 2, which were from EcoICRI-cut plasmid. Transcripts ending in A+ are polyadenylated. C, capped transcript; U, uncapped transcript.

Figure 8A:
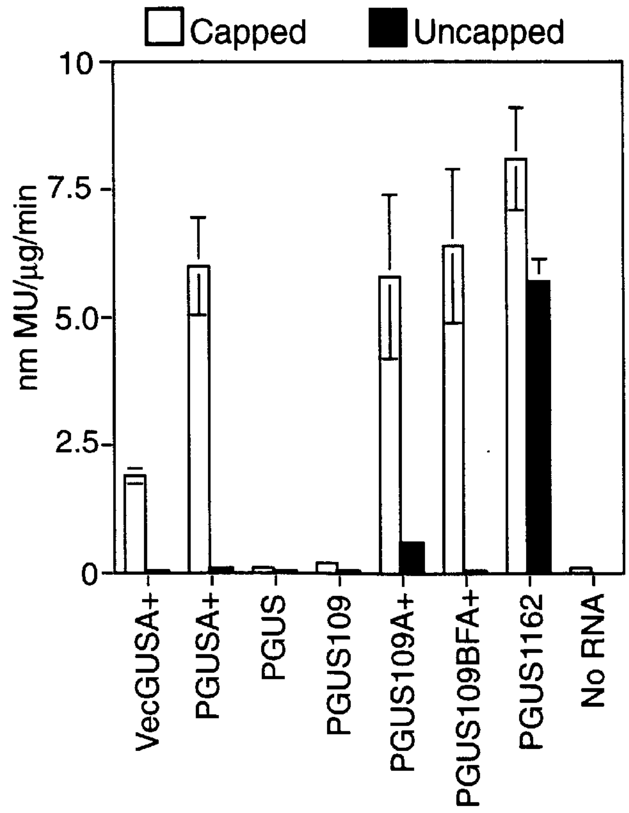
Figure 8B:
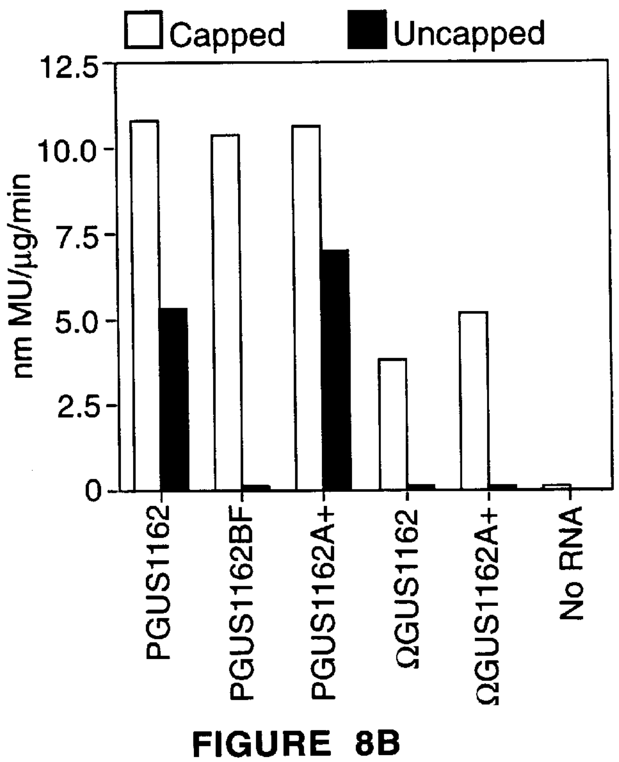
Figure 8C:
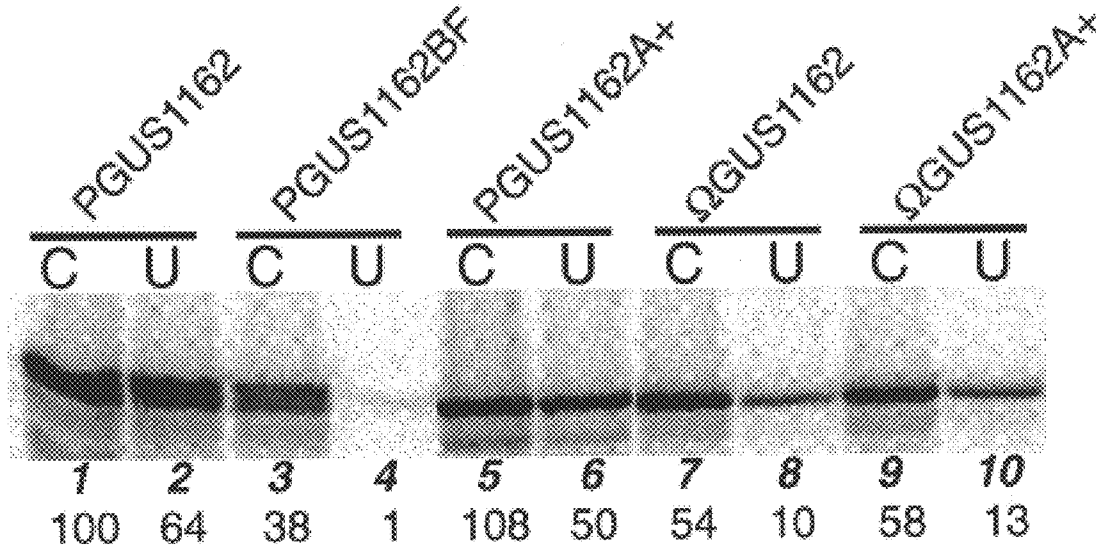

FIGS. 8A and 8B show GUS expression in protoplasts electroporated with transcripts containing various 5' and 3' UTRs. GUS activity is measured in nmoles (nm) of methylumbelliferone (MU) produced per μg of cellular protein per min in a 2 hr reaction. Transcripts containing a poly(A) tail (A+) are from EcoRI-linearized plasmids; others are from plasmids linearized with SmaI. Transcript PGUS is from EcoICRI-linearized pPGUS109. In panel A, data represent averages (+/− SD) from three separate experiments, each of which was performed in duplicate. In panel B, data represent averages from two separate experiments each of which was performed in duplicate. FIG. 8C shows wheat germ translation products of transcripts used in panel B were analyzed and quantitated. C, capped; U, uncapped transcript.

Figure 9A:
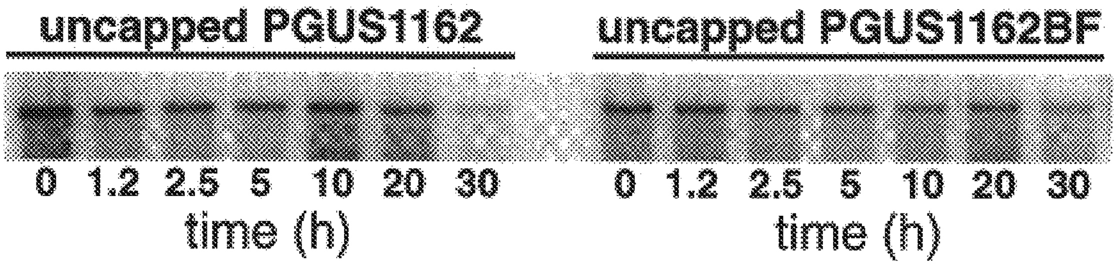
Figure 9B:
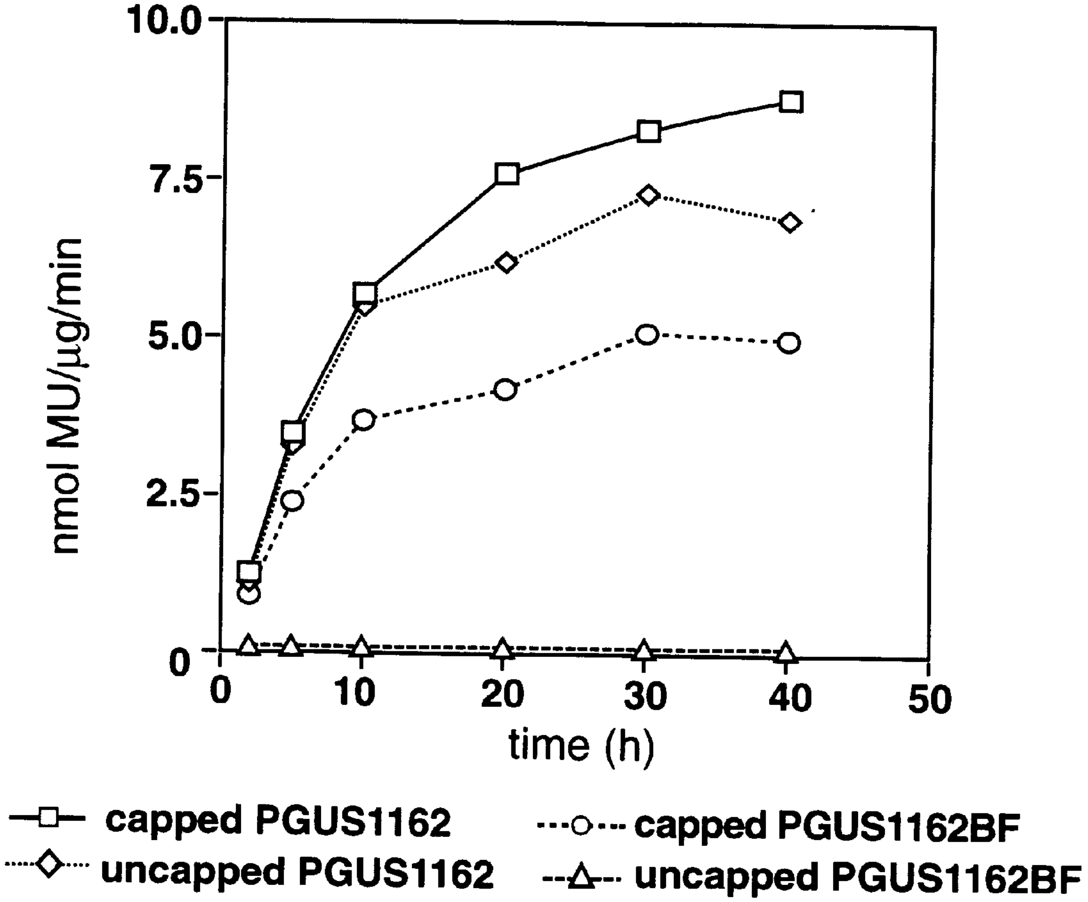

FIGS. 9A and 9B show the relative stability of mRNAs electroporated in oat protoplasts. FIG. 9A shows Southern blot hybridization detecting uncapped transcripts isolated from oat protoplasts at the indicated times after electroporation. The blot was hybridized with $^{32}P$-labeled antisense GUS transcript. FIG. 9B shows the kinetics of GUS enzymatic activity accumulation at indicated times after electroporation of oat protoplasts. The GUS assay was performed as described above.

Figure 10:
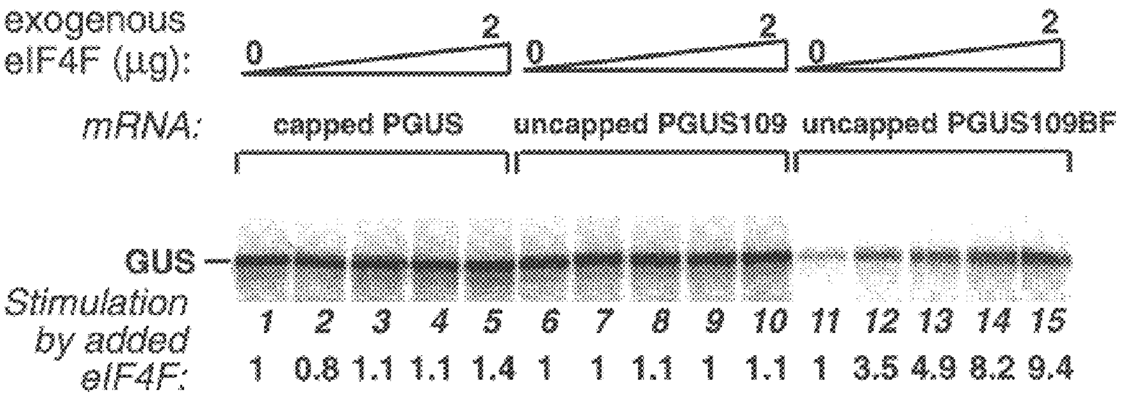

FIG. 10 shows the effect of added eIF4F on translation of capped and uncapped mRNAs containing or lacking the functional 109 3'TE in wheat germ extract. PGUS transcript was prepared by in vitro transcription from pPGUS109 that had been linearized with EcoICRI which removes the 3'TE. PGUS109 was prepared from the same plasmid linearized with EcoRI. Transcript PGUS109BF is from the BamHI-filled mutant of pPGUS109 (pPGUS109BF), linearized with EcoRI. Translation reactions were performed. Amount of added initiation factor: lanes 1,6,11: 0; lanes 2,7,12: 0.25 (g; lanes 3, 8, 13: 0.5 (g; lanes 4, 9, 14: 1.0 (g; lanes 5, 10, 15: 2.0 μg. The translation efficiency of each mRNA with no exogenous translation factor was defined as 1.

Figure 11A:
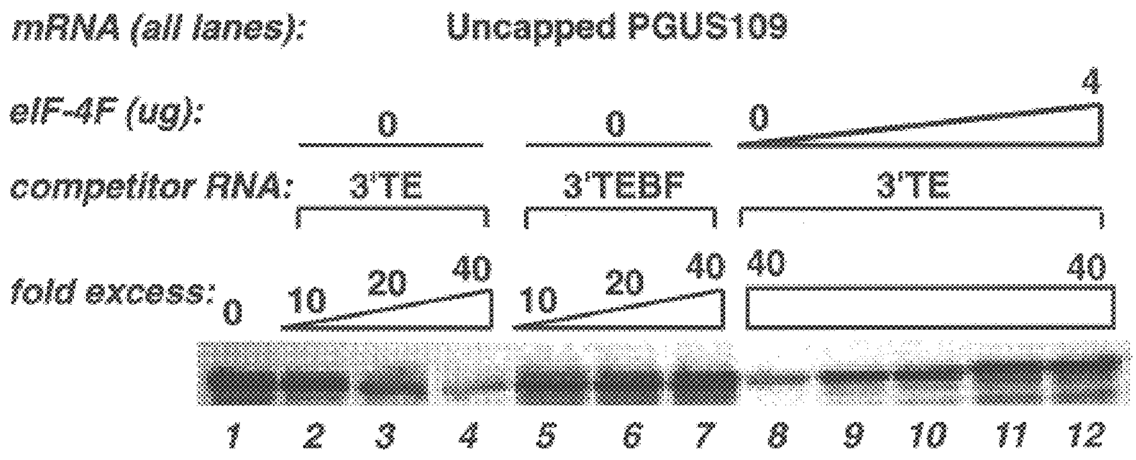
Figure 11B:
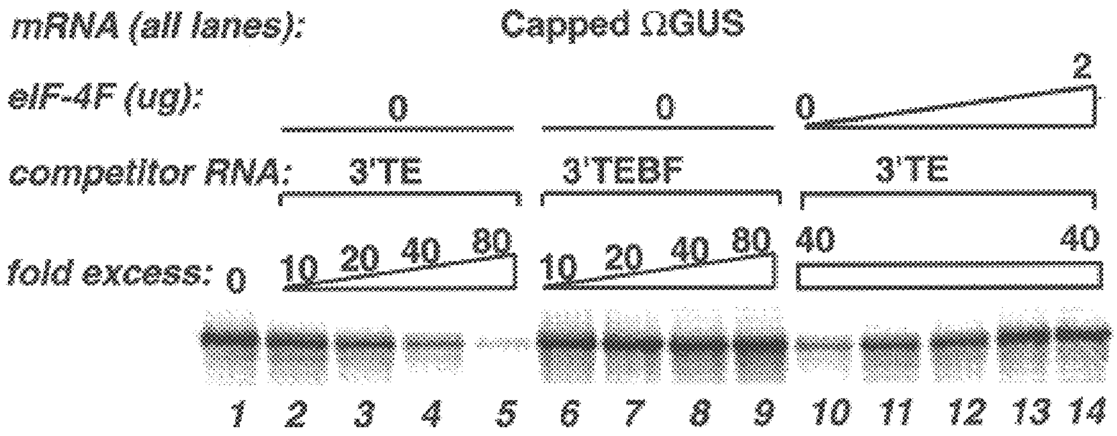

FIGS. 11A and 11B show the inhibition of translation by the 109 nt 3'TE in trans, and restoration by eIF4F. Uncapped PGUS109 (panel A) or capped (GUS (panel B) mRNAs (0.1 pmole) were translated in wheat germ extracts, with indicated amounts of added transcript comprising the 109 nt 3'TE (3'TE), or mutant 3'TE with the GAUC duplication at the BamHI site (3'TEBF) as competitor RNA. Amount of eIF4F added: panel A lanes 1–8: none; lanes 9–12: 0.5, 1.0, 2.0 and 4.0 (g, respectively; panel B lanes 1–10: none; lanes 11–14: 0.25, 0.5, 1.0 and 2.0 μg, respectively. The 109 nt 3'TE RNA and 109 nt 3'TEBF RNA were synthesized in uncapped form from SmaI-linearized p3'TE and p3'TEBF, respectively. Translation was performed in wheat germ extracts.

Figure 12A:
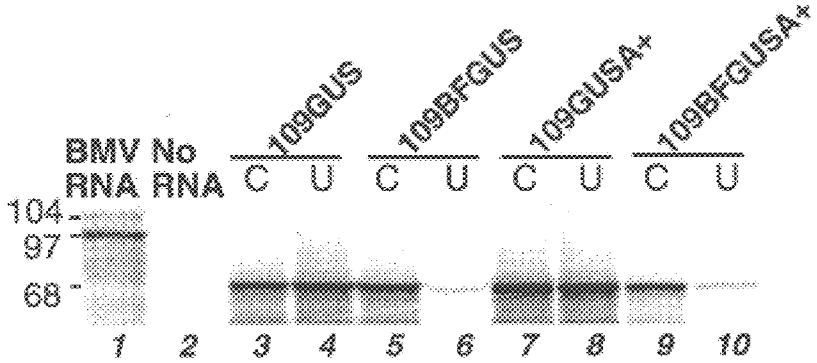
Figure 12B:
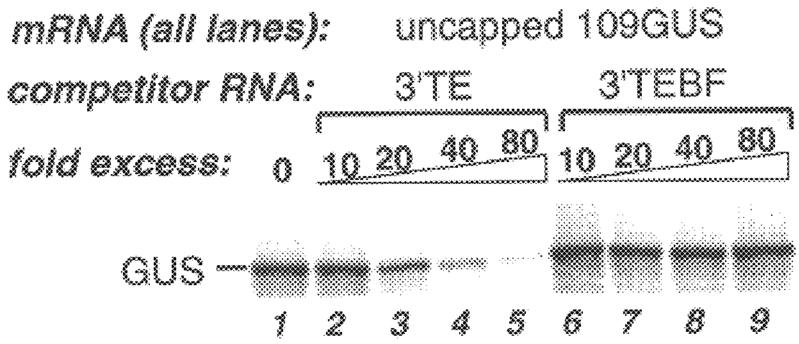
Figure 12C:
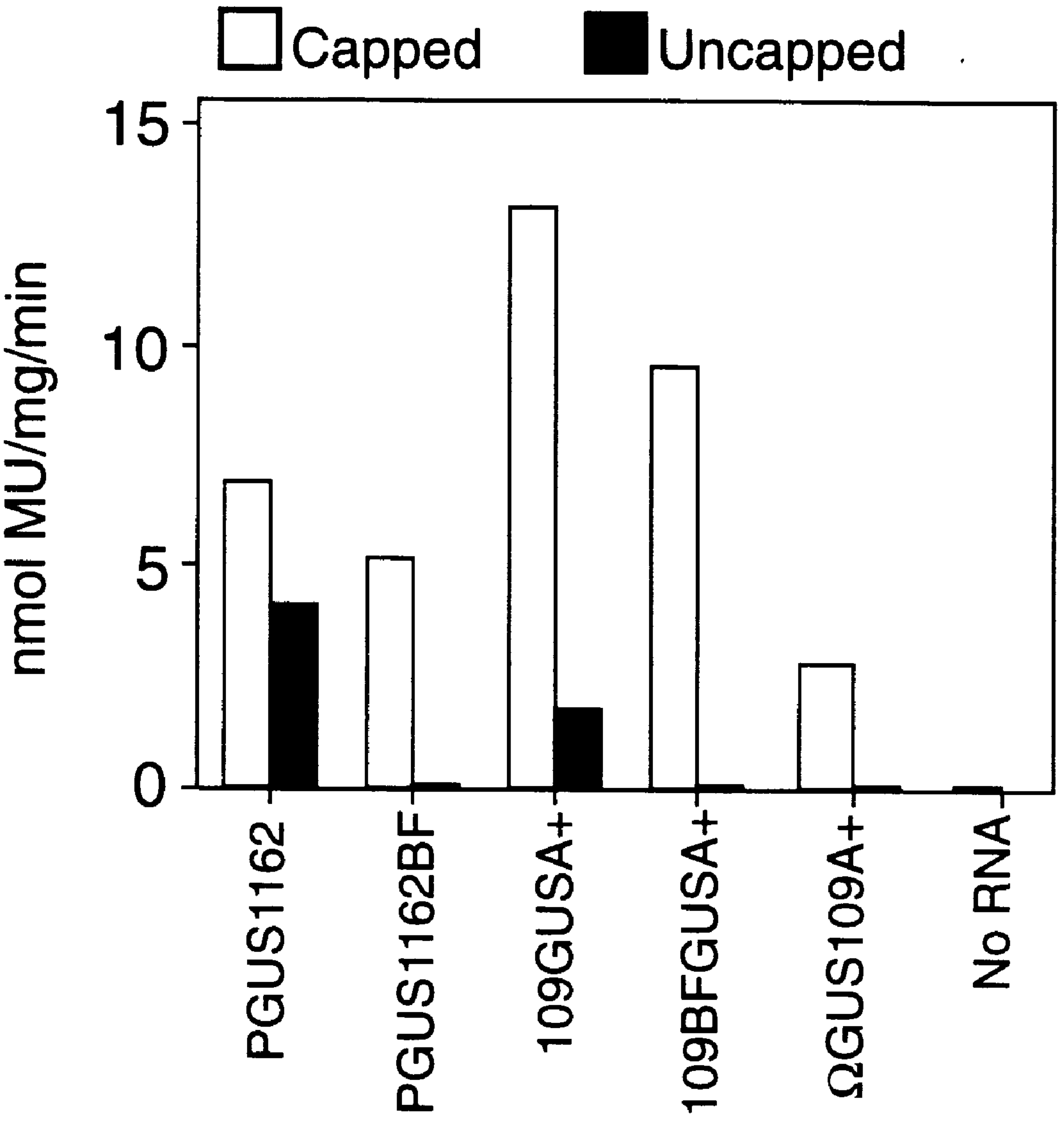

FIGS. 12A–C show the translation of transcripts having the 109 nt 3'TE in place of the viral 5'UTR upstream of the GUS ORF. FIG. 12A shows the in vitro translation in wheat germ extracts. Prior to transcription, templates for transcripts in lanes 3–6 were linearized with XbaI, and templates for transcripts in lanes 7–10 were linearized with EcoRI, resulting in the poly(A) tail indicated by A+. FIG. 12B shows the effect of addition of the 109 nt 3'TE or 109 nt 3'TEBF transcripts in trans on translation of uncapped 109GUS in wheat germ extracts. 109GUS RNA was transcribed from XbaI-cut p109GUSA. FIG. 12C shows the GUS activity from the indicated transcripts 20 hr after electroporation into oat protoplasts, assayed as described above.

FIG. 13 shows the alignments of portions of 3'UTRs of viral genomes showing their locations between the 3'-proximal confirmed gene (encodes a structural protein in all cases) and the 3' end of the genome. Underlined bases of consensus (bold) are complementary to the conserved sequence 5–10 bases from the 3' end of 18S rRNA. Underlined bases in STNV RNA have been proposed to base-pair to a nearby, nonoverlapping region of 18S rRNA (Danthinne et al., 1993). Vertical bars indicate locations of additional bases (below line) which are looped out in order to optimize alignments. In addition to the BYDV-PAV sequence of the given accession number, ten other BYDV-PAV isolates share this sequence. Abbreviations not used in text: BYDV-MAV, the MAV BYDV; TNV-A and -D, the A and D strains of TNV; SCNMV1, RNA 1 of sweet clover necrotic mosaic virus; CRSV1, RNA 1 of carnation ringspot virus; Luteo I, subgroup I luteovirus; Necro, necrovirus; Diantho, dianthovirus.

Figure 14A:
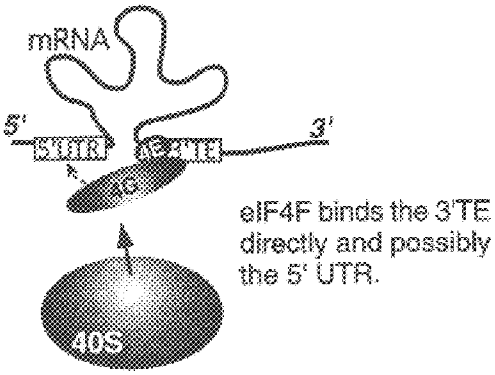
Figure 14B:
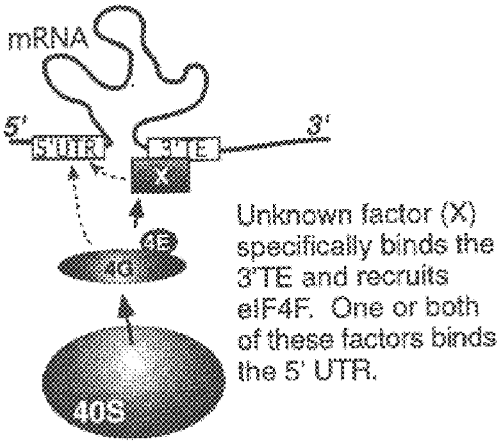
Figure 14C:
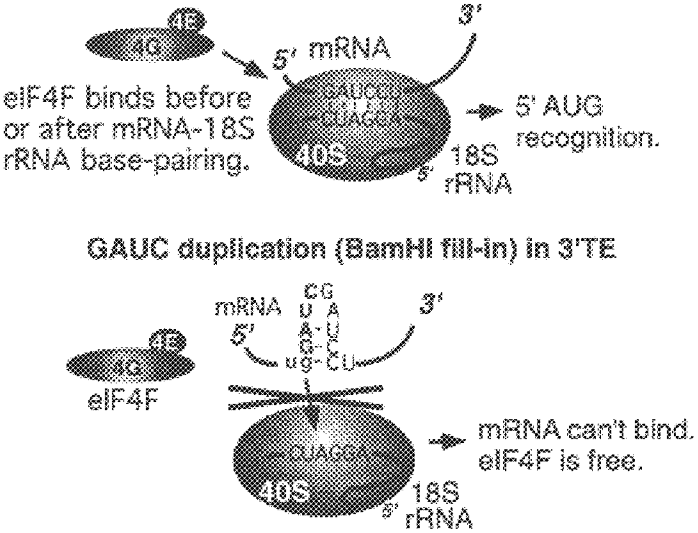

FIGS. 14A–C show the possible models for ribosome recruitment by the 3'TE consistent with the data presented. FIG. 14A shows the eIF4F (consisting of subunits eIF4E and eIF4G) specifically binds the 3'TE with high affinity, recruits the 40S subunit as it does in normal cap-dependent translation, and perhaps with participation of other factors, recognizes the 5'UTR. FIG. 14B shows an unknown factor (X) specifically binds the 3'TE, and possibly the 5'UTR, prior to recruiting eIF4F. Subsequent events occur as in panel B. FIG. 14C shows the portion (underlined in FIG. 7) of the conserved region in the 3'TE (mRNA) base-pairs directly to the conserved bases 5–10 nt upstream of the 3' end of 18S rRNA. This base-pairing may be facilitated by eIF4F (shown as its subunits eIF4E and eIF4G), or eIF4F may bind after the mRNA base-pairs to the 18S RNA. Following this binding, the ribosome is delivered to the 5' end of the mRNA by a mechanism not shown, perhaps by eIF4F. eIF4F (and other factors ) then participates in scanning until the first AUG is detected, at which polypeptide synthesis initiates. The GAUC duplication at the BamHI site disrupts base-pairing to 18S rRNA perhaps by formation of the alternative secondary structure shown or by others. eIF4F either does not recognize the mutated 3'TE, or it does not bind because the mRNA never base-pairs to the 18S RNA.

DETAILED DESCRIPTION OF THE INVENTION

Recombinant genes for producing proteins in plants comprise in sequence the following operably linked elements: a promoter which functions in plants, a structural gene encoding the target protein, and a non-translated region which also functions in plants to cause the addition of polyadenylated nucleotides to the RNA sequences. Much effort has been directed recently to improving recombinant plant gene expression. For example, improved recombinant plant genes have been generated by using stronger promoters, e.g., certain plant virus promoters. Expression of recombinant plant genes has also been improved by the optimization of the non-translated leader sequences.

The present invention discloses the identification of two regions on the genomic RNA of barley yellow dwarf virus, PAV serotype (BYDV-PAV): bases 1–168 (the entire 5'UTR plus first 9 codons of the 39K open reading frame), and 4513–5677 which, when placed in the 5' and 3' untranslated regions (UTRs), respectively, confer the ability of an mRNA to be translated efficiently in the absence of a 5' cap structure. (Base numbering is from Miller et al., 1988). mRNAs with these sequences are expressed with equal, and very high, efficency whether or not they contain a 5' cap structure, and at least 100-fold more efficiently than uncapped RNA lacking these sequences. Bases 4814–4922 (3'TE) in the 3'UTR were sufficient to confer cap-independent translation in vitro in wheat germ extracts but gave only partial stimulation of translation of uncapped RNA in vivo (oat cells), and also required a poly(A) tail in vivo. The present invention discloses that the presence of the entire 3'-terminal 1164 bases of the barley yellow dwarf virus-PAV genome gives 10–15-fold more expression from uncapped mRNA, than the smaller 3'TE, and no poly(A) tail was necessary.

The ability to translate uncapped RNAs is a valuable tool for high level expression of genes in transgenic plants. In eukaryotes, all genes that encode proteins, i.e., that produce mRNAs, are transcribed by DNA-dependent RNA polymerase II. In the process of transcription, i.e., the synthesis of mRNA, a 5' cap structure is added to the RNA. Promoters for RNA polymerase I (for ribosomal RNAs) and RNA polymerase III (for tRNAs and a ribosomal RNA) can have many applications, and are much more active (produce more RNA transcript) than polymerase II promoters. The RNA resulting from these promoters is not capped or polyadenylated, so normally it would not be translatable.

The barley yellow dwarf virus-PAV cap-independent translation sequences could facilitate expression of genes from promoters other than those recognized by RNA polymerase II. The barley yellow dwarf virus-PAV sequences preclude the need for a 5' cap, and a poly(A) tail can be included directly in the gene sequence if necessary. Thus, the barley yellow dwarf virus-PAV sequences could allow RNA from these promoters for polymerases I and III to be translated efficiently in vivo. There is significant demand for very high level expression of proteins in plants. The ability to use polymerase I or III promoters to produce enormous amounts of translatable mRNA could fill this need.

The present invention also specifically contemplates the use of the methods disclosed herein with bacteriophage promoters. Promoters such as that of gene 10 of bacteriophage T7 are extremely active, producing very large amounts of RNA. The bacteriophage polymerase that recognizes this promoter would be expressed from a separate gene in the host cell. This approach has been used in *E. coli* for extremely high expression of defined proteins, e.g., the pET system, Novagen, Madison, Wis.). However, T7 polymerase transcripts are uncapped.

In mammalian cells, a cap-independent translation signal from a mammalian virus has been used for this purpose. The 5' UTR (Internal Ribosome Entry Site) of a picornavirus has been used to facilitate efficient translation of the resulting RNAs (Dunn et al., 1988). The IRES sequences of picornaviruses are very powerful, well-characterized facilitators of translation of uncapped RNAs (McBratney et al., 1993). The same strategy can be used in plants with the translation enhancing sequences of barley yellow dwarf virus-PAV (instead of the mammalian viral IRES) flanking the gene to be expressed at high levels. The plants would also be transformed with the bacteriophage polymerase gene, in such a way that the polymerase would accumulate in the nucleus. The gene would then be transcribed by the T7 polymerase that recognizes the T7 promoter linked to the gene of interest. Transgenic plants that accumulate T7 polymerase in the nucleus have been constructed (Lassner et al., 1991; Caviedes et al., 1994). This T7 approach, without the barley yellow dwarf virus-PAV sequences, and with limited success, has been reported (Tuttle, 1994; Caviedes, 1994).

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid described herein are preferred to be in the "L" isomeric form. In keeping with standard polypeptide nomeclature, *J Biol. Chem.,* 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |

-continued

| TABLE OF CORRESPONDENCE | | |
|---|---|---|
| SYMBOL | | |
| 1-Letter | 3-Letter | AMINO ACID |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxyterminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an automous unit of DNA or RNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in tis either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" or "coding region" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The terms "cap", "capped" and "uncapped" as used herein, shall refer to the structural modification at the 5' end of eukaryotic RNAs transcribed by RNA polymerase II received prior to leaving the nucleus. The cap is an added 5' terminal G, methylated on the 7-position of the purine base and linked to the initiating nucleotide by a 5'—5' triphosphate linkage.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the mdia, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or a common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Thus, the present invention is directed to method of increasing the production of a protein translated from an uncapped eukaryotic messenger ribonucleic acid (mRNA), comprising the steps of: selecting a nucleotide sequence encoding a protein to be expressed; joining nucleotides 1–168 of the barley yellow dwarf virus RNA, PAV serotype to the 5' untranslated region of said uncapped mRNA, said nucleotides 1–168 comprising the 5' untranslated region plus first 27 nucleotides of the open reading frame of the barley yellow dwarf virus RNA; linking nucleotides 4513–5677 of the barley yellow dwarf virus RNA, PAV serotype, to the 3' untranslated region of said uncapped mRNA; and expressing the protein. Representative examples of uncapped eukaryotic mRNA which for proteins whose translation can be enhanced include those coding for pharmaceutical peptides such as insulin or other peptide hormones, vaccines, or antibodies, industrial enzymes, altered seed storage proteins with improved amino acid composition, insect toxins, pathogen-derived and host-derived disease resistance genes.

The present invention is also directed to a DNA molecule which comprises: (a) a promoter region which functions in plant cells to cause the production of an RNA sequence, which is operably linked to (b) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA; (c) a structural DNA sequence, wherein said structural DNA sequence is heterologous to said 5' untranslated region, which is operably linked to (d) a 3' untranslated region that functions in plant cells to cause the termination of transcription, said 3' untranslated region comprising nucleotides 4513–5677 of the barley yellow dwarf virus RNA. Representative examples of useful promoters include bacteriophases such as T7 (requires corresponding bacteriophage polymerase), polymerase III, and polymerase I.

Furthermore, the present invention is also directed to a method for providing enhanced gene expression in plants which comprises: (a) transforming plant cells with a DNA molecule which comprises: (i) a promoter region which functions in plant cells to cause the production of an RNA sequence, which is operably linked to (ii) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA; (iii) a structural DNA sequence, wherein said structural DNA sequence is heterologous to said 5' untranslated region, which is operably linked to (iv) a 3' untranslated region that functions in plant cells to cause the termination of transcription, said 3' untranslated region comprising nucleotides 4513–5677 of the barley yellow dwarf virus RNA; (b) selecting said plant cells which have been transformed; (c) regenerating said plant cells to provide a differentiated plant; and (d) selecting a transformed plant which expresses said structural gene.

The present invention is also directed to a method of increasing the production of a protein translated from an uncapped eukaryotic messenger ribonucleic acid (mRNA), comprising the steps of: selecting a nucleotide sequence encoding a protein to be expressed; joining nucleotides 4817–4925 of the barley yellow dwarf virus RNA, PAV serotype to the 5' untranslated region of said uncapped mRNA; and expressing the protein. Representative uncapped eukaryotic mRNA include those coding for peptide hormones, vaccines, antibodies, industrial enzymes, altered seed storage proteins, insect toxins, pathogen-derived and host-derived discase resistance genes.

The present invention is also directed to a DNA molecule which comprises: (a) a promoter region which functions in plant cells to cause the production of an RNA sequence, which is operably linked to (b) a 5' untranslated region including a 5' translation enhancing segment, said 5' translation enhancing segment comprising nucleotides 4817–4925 of the barley yellow dwarf virus RNA, PAV serotype; (c) a coding sequence, wherein said coding sequence is heterologous to said 5' untranslated region, which is operably linked to(d) a 3' untranslated region that functions in plant cells to cause the termination of transcription.

The present invention is also directed to a method for providing enhanced gene expression in plants which comprises: (a) transforming plant cells with a DNA molecule which comprises: (i) a promoter region which functions in plant cells to cause the production of an RNA sequence, which is operably linked to (ii) a 5' untranslated region including a 5' translation enhancing segment, said 5' translation enhancing segment comprising nucleotides 4817–4925 of the barley yellow dwarf virus RNA, PAV serotype; (iii) a coding sequence, wherein said coding sequence is heterologous to said 5' untranslated region, which is operably linked to (iv) a 3' untranslated region that functions in plant cells to cause the termination of transcription; (b) selecting said plant cells which have been transformed; (c) regenerating said plant cells to provide a differentiated plant; and (d) selecting a transformed plant which expresses said gene.

The following examples are given for the purpose of illustrating various embodiments of the invention and are not meant to limit the present invention in any fashion.

EXAMPLE 1

Methods pCIGUS, pVecGUSA and pGUSEA were described in Wang, S., et al., *J. Biol. Chem.,* 270:13446–13452, (1995). Briefly, pCIGUS was made so that the β-glucuronidase coding sequence was flanked by the 5' terminal 169 nucleotides of barley yellow dwarf virus-PAV RNA at its 5' end and bases 4513–5677 in its 3'-UTR. The clone pPAVGUSRTS which contains the β-glucuronidase gene including an upstream multiple cloning site from pAGUS 1 inserted between bases 3477 and the $ScaI_{4513}$ site in pPAV6. pPAVGUSRT8 was digested with Eco-47 $III_{169}$ and Bsp120 I (codon 5 of the β-glucuronidase ORF). This was blunt ended with T4 polymerase and religated to produce pCIGUS. In pCIGUS, the entire 5'-UTR and the first nine codons of the β-glucuronidase coding sequence were derived from the first 169 nucleotides of barley yellow dwarf virus-PAV RNA. The ScaI site was destroyed in the process, so pCIGUS was linearized at a unique EcoICR I site in the β-glucuronidase-derived portion of the 3'-UTR to generate transcripts lacking sequences in the 3'-UTR.

pT7 GUSA(+) was constructed to add a poly(A) tail to the β-glucuronidase 3'-UTR. pT7 GUS1 was first digested with SmaI and ScaI. Then the fragment containing the β-glucuronidase gene was gel purified and ligated to SmaI-ScaI-digested pSP64poly(A) (Promega), which has a run of 30 adenosine residues between the SmaI and EcoRI sites in its multiple cloning site. pGUSEA1 was made by cloning the PstI-EcoICR I fragment of pCIGUS that spans the T7 promoter, the first 169 nucleotides of barley yellow dwarf virus-PAV genomic RNA and the β-glucuronidase coding region into pSP64poly(A) cut with the same enzymes.

To construct pCIGUSA, the poly(A)-containing, SmaI-PvuII-fragment of pSP64poly(A) was cloned into SmaI-cut pCIGUS. pGUS109A was derived from pGUSEA1. First, a sequence corresponding to the fragment of 109 bases in the 3' untranslated region of PAV genome (nucleotide 4817 to nucleotide 4925) was amplified by PCR using primers: 5'GCGGAGCTCAGACAACACCACTAGCAC3' (SEQ ID No. 1) and 5'GCGGAGCTCCATCGGCCAAACACAATAC3' (SEQ ID No. 2). The product was cut with SacI (underlined) and ligated into SacI-digested pGUSEA1. To construct pGUS109, the amplified 109 base fragment from PAV6 was inserted into SacI-digested pGEM3Zf(+) giving rise to pT7 -109. Then the SmaI-EcoRI fragment from pT7 -109 was ligated to EcoICRI-EcoRI-digested pGUS109A. Plasmids containing the GATC duplication at the $BamHI_{4837}$ site (BF) were constructed by cutting, Klenow-filling[25] and re-ligating the BamHI site. pΩCIGUSA was constructed via a series of intermediate plasmids. A fragment corresponding to the Ω sequence and 5' end of the *E. coli uidA* coding region was PCR amplified from pAGUS-Tn2 [26] with the primers: 5'GCGGCGGCCGCTAATACGACTCACTATAGGTATTTTTACAAC 3' (SEQ ID No. 3) and 5'TCGCGATCCAGACTGAATGC 3' (SEQ ID No. 4). Following digestion with NotI (underlined) and NcoI (internal), the amplified fragment was cloned into NotI-NcoI-cut pSL1180 (Pharmacia) giving rise to pSLΩ2. To construct pSLΩGUSA, the *E. coli uidA* gene and poly(A) tail was subcloned from pVecGUSA into the NcoI and EcoRI sites of pSLΩ2. The Csp45I-EcoRI fragment of pCIGUSA was cloned into similarly-cut pSLΩGUSA, resulting in pΩCIGUSA. All constructs were verified by direct DNA sequencing.

Oat protoplasts were prepared, electroporated, cultured and *E. coli uidA* activity was determined as described in Dinesh-Kumar, S. P., et al., *Plant Cell,* 5:679–692, (1993), except that 30 pmol (subsaturating amounts) of the indicated transcripts were used instead of DNA. Cells were assayed 24 hours after electroporation, at which time *E. coli uidA* activity was still accumulating linearly.

EXAMPLE 2

To map the 3' translation enhancer more precisely, the ability of smaller portions of this region to stimulate translation of uncapped mRNA in wheat germ translation extracts was demonstrated. The mRNAs used herein (FIG. 1A) are in vitro transcripts comprising the *E. coli uidA* (GUS) gene flanked by various 5' and 3' untranslated regions. Uncapped *E. coli uidA* mRNA that harbors the 109 nucleotide sequence from the intergenic region between PAV open reading frames 5 and 6 (bases 4817–4925) in its 3' untranslated region was translated with the same efficiency as transcripts of pCIGUS (FIG. 1B, lanes 3–4), which contain the larger (500 nucleotide) 3' translation enhancer sequence identified previously[13]. GUS 109 RNA with the 3' translation enhancer yielded 40–50 fold more *E. coli uidA* protein than 3' translation enhancer-lacking transcript (FIG. 1B, compare lanes 2 and 3). 5' or 3' truncation at the BamHI4837 site in the 3' translation enhancer[13] or truncation 3' of nucleotide 4873 (data not shown) eliminated 3' translation enhancer activity. A four base duplication (GAUC) within the BamHI4837 site (GUS109BF) destroyed cap-independent translation (FIG. 1B), indicating the specificity of the sequence that stimulates translation. Addition of a 5' cap stimulated translation of these transcripts by 40-fold, to a similar level observed for uncapped, 3' translation enhancer-containing GUS109. A poly(A) tail had little effect on translation of any transcripts in wheat germ translation extracts (FIG. 1B).

EXAMPLE 2

To assess the effects of the 3' translation enhancer in vivo, *E. coli uidA*-encoding transcripts were electroporated into oat protoplasts and their mRNA activities measured by assaying for *E. coli uidA* activity. A control transcript VecGUSA, containing a multiple cloning site-derived 5' untranslated region, a 30 nucleotide poly(A) tail and no 5' cap yielded no significant *E. coli uidA* activity, whereas the capped form expressed *E. coli uidA* at 50-fold above background (FIG. 2A). Replacement of the 5' untranslated region with that from PAV stimulated *E. coli uidA* expression from capped mRNA 3-fold further, in agreement with results observed in wheat germ translation extractsl[13].

The presence of the 109 nucleotide 3' translation enhancer (in the absence of poly(A)) gave only background levels of *E. coli uidA* from uncapped transcript, and only slightly above background levels on capped transcripts (FIG. 2A). The combination of both the 109 nucleotide 3' translation enhancer and a poly(A) tail resulted in significant translation (10-times background) of uncapped *E. coli uidA* mRNA. Presence of a 5' cap on this transcript stimulated *E. coli uidA* expression by another order of magnitude. This differed from the wheat germ translation extracts system in which the 109 nucleotide 3' translation enhancer stimulated translation by at least 40-fold to the level conferred by a 5' cap (FIG. 1B), and in which a poly(A) tail was unnecessary. This requirement for a poly(A) tail in vivo but not in vitro agrees with previous reports[5].

EXAMPLE 3

To test whether PAV RNA sequences outside the 109 nucleotide 3'translation enhancer were needed in vivo to obtain the level of stimulation seen in vitro, the sequence from nucleotide 4513 to the 3' end of the genome, (nucleotide 5,677) was placed in the 3' untranslated region of a *E. coli uidA*-encoding transcript. Uncapped transcript (CIGUS-Sm) from this plasmid gave *E. coli uidA* activity 100-times background (FIG. 2A), in the same range as capped, polyadenylated transcript containing the 109 nucleotide 3' translation enhancer. Addition of a cap to CIGUS-Sm stimulated expression less than two-fold, and a poly(A) tail was unnecessary. Thus, full stimulation of cap-independent translation requires more viral sequence in vivo than was needed in wheat germ translation extracts. The four-base duplication in the BamHI4837 site, abolished expression from uncapped transcript, verifying the specificity of the 3'translation enhancer effect (FIG. 2A). Addition of a 5' cap gave as much *E. coli uidA* expression as capped transcript containing the functional 3'translation enhancer. Thus, there is a sequence within the 109 nucleotide 3'translation enhancer necessary to substitute for a 5' cap, and sequence elsewhere in the 1163 nucleotide virus-derived 3' untranslated region may substitute for a poly(A) tail. Viral 3' untranslated region sequences have been shown previously to substitute for poly(A) tail function[6].

EXAMPLE 4

The role of the viral 5' untranslated region was tested by replacing it with the 5' untranslated region from tobacco mosaic virus (tobacco mosaic virus Ω sequence). This tobacco mosaic virus sequence stimulates translation of capped and uncapped mRNAs in vitro, but does not reduce cap dependence in vivo[16]. Substitution of the PAV 5' untranslated region with the tobacco mosaic virus Ω sequence abolished translation of uncapped mRNA in vivo, even in the presence of the 1163 nucleotide virus-derived 3' untranslated region (FIG. 2B), and increased its cap-dependence in vitro (FIG. 2C). Thus the 3'translation enhancer requires at least a portion of the PAV 5' untranslated region and does not stimulate translation by the same mechanism as tobacco mosaic virus Ω sequence. The fact that expression of the capped, poly(A)+, tobacco mosaic virus Ω sequence-containing mRNA is no higher than that of uncapped mRNA containing the full PAV 5' and 3' untranslated regions (CIGUS-Sm), demonstrates the very high levels of expression that are being obtained from uncapped CIGUS-Sm. This resembles in vitro studies of satellite tobacco necrosis virus for which base-pairing between 5' and 3' untranslated regions was predicted[14,15]. No obvious, phylogenetically conserved potential basepairing between untranslated regions of PAV RNA was detected.

EXAMPLE 5

If the 3' translation enhancer is required for viral gene expression, it should be essential for virus RNA replication. Thus, the effect of the GAUC duplication at base 4837 was tested in full-length genomic transcripts. As observed with the *E. coli uidA* mRNAs, this duplication drastically reduced translation of uncapped, full-length PAV genomic transcripts in vitro (FIG. 3A). The expected products of ORF1 and (by frameshifting) ORF2 were produced only in the presence of the wildtype 3' translation enhancer or a 5' cap. The wildtype (PAV6) RNA replicated efficiently in oat protoplasts, whereas the mutant (PAV6BF) transcript replicated poorly, if at all (FIG. 3B). Presence of a 5' cap did not restore replication activity to PAVBF, indicating that the progeny RNAs are unlikely to be capped. Capping actually reduced accumulation of PAV6 RNA (FIG. 3*b*) and virions[17]. Although these results do not exclude the possibility that the mutation is knocking out some other viral function, the results support the notion that the 3'translation enhancer plays an essential. role in translation of PAV RNA during replication.

A potential 18S ribosomal RNA binding sequence in the 3'translation enhancer of satellite tobacco necrosis virus was proposed to facilitate cap-indendent translation[15] by analogy with a proposed prokaryotic-like mechanism for ribosomal recognition of picornaviral IRES's[18]. A similar sequence, GAUCCU, complementary to the 3' end of wheat 18S rRNA is in an 18 nucleotide portion of the 3'translation enhancer that is highly conserved in the 5' ends of the 3' untranslated regions of all subgroup I luteoviruses including 10 PAV isolates, tobacco necrosis virus (TNV, the helper for satellite tobacco necrosis virus) and in RNA1's of dianthoviruses (FIG. 4). Like the infectious PAV6 transcript, TNV RNA lacks a 5' cap[19]. However, a dianthoviral RNA is reportedly capped[20]. Significantly, the GAUC duplication that inactivates the PAV 3'translation enhancer is in the 18 nucleotide sequence and immediately adjacent to the potential rRNA-binding sequence (FIG. 4). Thus, the GAUC could inactivate 3'translation enhancer function by disrupting 3'translation enhancer-18S rRNA interactions. The 18 nucleotide sequence is not well conserved in the 3'translation enhancer of satellite tobacco necrosis virus, but the computer alignment of the satellite tobacco necrosis virus 3'translation enhancer with the above viral RNAs also aligns the potential rRNA binding sequencesl[5] (FIG. 4).

The 3' translation enhancer may also facilitate initiation by recruiting initiation factors. Other 3' untranslated region sequences (poly(A) tails) have been reported to bind initiation factors eIF-4F and 4B[21] or poly(A) binding protein[22] to facilitate initiation at the 5' AUG, but this mechanism is clearly cap-dependent. Whether the 3'translation enhancer acts by recruiting initiation factors, ribosomes or both, communication with the 5' end of the RNA must occur. Because significant basepairing between 5' and 3' untranslated regions seems unlikely, a trans-acting factor(s) may bind these sequences to bring them together. An example of a protein likely to interact with both ends of an mRNA is vaccinia virus protein VP39 which participates in cap methylation and in stimulating polyadenylation[23]. The nature of 5'–3' communication factor(s) in uninfected eukaryotic cells and by what mechanism a 3' nucleotide sequence subsitutes for a 5' cap is determined.

EXAMPLE 6

In another embodiment of the present invention, the 109 nucleotide 3' translation enhancer (3' TE; the intergenic region between open reading frames 5 and 6 (bases 4817–4925), up to and including the ORF6 (start codon) was placed in the 5' untranslated region (5' UTR) of a heterologous gene and mediated efficient translation of uncapped mRNA. FIG. 5 illustrates that transcripts (called 5'TEGUS or 5'TEGUSA) containing this (and no other) sequence 5' of the GUS reporter gene start codon gave similar levels of translation from uncapped mRNA in wheat germ extracts to the constructs with the 5' and 3' UTSs derived from BYDV-PAV in which the 3' translation enhancer was in the 3' UTR.

FIG. 6 shows that when an uncapped mRNA containing the 3'translation enhancer in the 5' UTR as well as a poly(A) tail was electroporated into oat protoplasts, it gave at least 50% as much GUS activity (gene expression) as the construct (CIGUS═GUS1162) containing the BYDV-PAV 5' UTR and, in its 3' UTR, the 1162 bases of the 3' end of the viral genome, including the 109 nucleotide 3' translation enhancer and probably other sequence that substitutes for a poly(A) tail. There was a two-fold difference in gene expression between the construct with the 3'translation enhancer in the 5' UTR and that with large regions of BYDV-PAV RNA in 5' and 3' UTRs (CIGUS, the highest expresser). The 50-fold stimulation over background levels of GUS by the construct with the 3' translation enhancer in the 5' UTR (5'TEGUSA) was significant.

The fact that only a 109 nucleotide sequence is needed and it can be placed completely in the 5' UTR provides additional utility for the present invention. Construction of expression cassettes are much easier. Although TMV Ω and alfalfa mosaic virus translation enhancers are located in the 5' UTR, they are cap-dependent. The 5' UTR of tobacco etch virus stimulates translation of uncapped mRNA, but it is stimulated a further 15-fold by capping (Carrington and Freed, 1990).

The following references were cited in the specification above:

1. Kozak, M., *J Cell Biol,* 108:229–241, (1989).
2. Merrick, W. C., *Microbiol Rev,* 56:291–315, (1992).
3. Standart, N., et al., *Biochimie,* 76:867–879, (1994).
4. Jacobson, A., in *Translational Control* (eds. Hershey, J. W. B., Mathews, M. B. & Sonenberg, N.) 451–480 (Cold Spring Harbor Laboratory Press, Cold Spring Harbor, 1996).
5. Gallie, D. R., *Genes Dev,* 5:2108–2116, (1991).
6. Gallie, D. R., et al., *Genes Dev,* 4:1149–1157, (1990).
7. Munroe, D., et al., *Mol Cell Biol,* 10:3441–3455, (1990).
8. Decker, C. J., et al., *Trends Biochem Sci,* 19:336–340, (1994).
9. Pelletier, J., et al., *Nature,* 334:320–323, (1988).
10. Sarnow, P., in *Current Topics in Microbiology and Immunology* (Springer, Berlin, 1995).
11. Carrington, J. C., et al., *J. Virol.,* 64:1590–1597, (1990).
12. Jackson, R. J., et al., *RNA,* 1:985–1000, (1995).
13. Wang, S., et al., *J. Biol. Chem.,* 270:13446–13452, (1995).
14. Timmer, R. T., et al. *J. Biol. Chem.,* 268:9504–9510, (1993).
15. Danthinne, X., et al., *Mol Cell Biol,* 13:3340–3349, (1993).
16. Sleat, D. E., et al., *Crc Press, Boca Raton,* (1992).
17. Dinesh-Kumar, S. P. in *Molecular, Cellular and Developmental Biology* (Iowa State University, Ames, 1993).
18. Pilipenko, E. V., et al. *Cell* 68, 119–131, (1992).
19. Lesnaw, J.A., et al., *Proc. Natl. Acad. Sci. USA,* 66:140–145, (1970).
20. Xiong, Z., et al., *Virology,* 171:543–554, (1989).
21. Gallie, D. R., et al., *J. Biol. Chem.,* 269:17166–17173, (1994).
22. Tarun, S. Z., et al., *Genes & Development,* 9:2997–3007, (1995).
23. Schnierle, B. S., et al., *Proc. Natl. Acac. Sci. USA,* 89:2897–2901, (1992).
24. Miller, W. A., et al., *Nucleic Acids Res.,* 16:6097–6111, (1988).
25. Sambrook, J., et al., *Molecular Cloning, a laboratory manual: 2nd edition* (Cold Spring Harbour Laboratory Press, Cold Spring Harbour, N.Y., 1989).
26. Skuzeski, J. M., et al., *Plant Molec.Biol.,* 15:65–79, (1990).
27. Dinesh-Kumar, S. P., et al., *Plant Cell,* 5:679–692, (1993).
28. Di, R., et al., *Molec.Plant-Microbe Interact.,* 6:444–452, (1993).
29. Mohan, B. R., et al., *Virology,* 212:186–195, (1995).
30. Chaloub, B. A., et al., *Archives of Virology,* 139:403–416, (1994).

EXAMPLE 7

A viral sequence in the 3' untranslated region mimics a 5' cap in stimulating translation of uncapped mRNA For recognition by the translational machinery, most eukaryotic cellular messenger RNAs have a 5' cap structure (e.g. $m^7G(5')ppp(5')N$). The present invention further describes a translation enhancer sequence (3'TE) located in the 3' untranslated region (UTR) of the genome of the PAV barley yellow dwarf virus (BYDV-PAV) which stimulates translation from uncapped mRNA by 30–100 fold in vitro and in vivo to a level equal to that of efficient capped mRNAs. A four base duplication within the 3'TE destroyed the stimulatory activity. Efficient translation was recovered by addition of a 5' cap to this mRNA. Translation of both uncapped mRNA containing the 3'TE in cis and capped mRNA lacking any BYDV-PAV sequence was inhibited specifically by added 3'TE RNA in trans. This inhibition was reversed by adding initiation factor 4F (eIF4F), suggesting that the 3'TE, like the 5' cap, mediates eIF4F-dependent translation initiation. The BYDV-PAV 5' UTR was necessary for the 3'TE to function, except when the 3'TE itself was moved to the 5' UTR. Thus, the 3'TE is sufficient for recruiting the translation factors and ribosomes, while the viral 5'UTR may serve only for the long distance 3'–5' communication. Models are proposed to explain this novel mechanism of cap-independent translation initiation facilitated by the 3'UTR.

The present invention demonstrates that genomic RNA of the PAV barley yellow dwarf virus (BYDV-PAV) harbors a sequence in the 3'UTR that confers cap-independent translation initiation at the 5' AUG of the mRNA in wheat germ extracts. The BYDVs are ubiquitous, economically important viruses of small grains. BYDV-PAV is a subgroup I luteovirus, whereas some other BYDVs are members of the very divergent subgroup II. The mechanism of translation initiation of BYDV-PAV is remarkable because the 3' translation enhancer (3'TE) that confers cap-independent translation is located five kilobases downstream, and is separated by several large untranslated open reading frames from the initiation codon. Furthermore, unlike other translational control elements in the 3'UTR, such as poly(A) tails, the 3'TE controls initiation at the 5' AUG in the absence of a 5' cap. The only other mRNA known to resemble this, in function, is satellite tobacco necrosis virus (STNV) RNA. This RNA differs from BYDV-PAV in that its 3' stimulatory element is located immediately 3' of the only ORF on the RNA, and 600 nucleotides downstream of the initiator AUG. The stimulatory elements of BYDV-PAV and STNV RNAs share no obvious sequence homology. For both RNAs, cap-independent translation has been reported only in cell-free extracts. Like capped mRNAs, STNV RNA translation depends on eIF4F or eIFiso4F, but the amount of factor needed for maximal translation is one tenth of that needed for capped mRNAs.

The present invention localizes the 3'TE to a smaller region in the BYDV-PAV genome, shows that it functions in vivo but requires more of the 3'UTR than in wheat germ extracts, provides evidence that the 3'TE facilitates initiation in an eIF4F-dependent manner, and shows that the translation initiation and 3'–5' communication functions can be uncoupled. These data shed light on possible mechanisms for a 3'UTR in mediating translation initiation.

EXAMPLE 8

Plasmid Construction

All constructs were verified by automated DNA sequencing. pGUS1162, pGUSA and pVecGUSA (formerly pCIGUS, pGUSEA and pT7 GUSA(+), respectively). To construct pGUS1162A, the $(A)_{30}$-containing, SmaI-PvuII-fragment of pSP64poly(A) (Promega) was cloned into SmaI-cut pGUS1162. pGUS109A was derived from pGUSA. First, the 109 nt sequence corresponding to BYDV-PAV bases 4817 to 4925) was amplified from pGUS1162 by PCR using primers: 5'GCGGAGCTCAGACAACACCAC TAGCAC 3' (SEQ ID No. 1) and 5'GCG GAGCTCCATCGGCCAAACACAATAC 3' (SEQ ID No. 2). The product was cut with SacI (underlined, an isoschizomer of EcoICRI) and ligated into SacI-digested pGUSA. To construct pGUS109, the amplified 109 base fragment was inserted into SacI-digested pGEM3Zf(+) giving rise to p3'TE. Then the SmaI-EcoRI fragment from p3'TE was ligated to EcoICRI-EcoRI-digested pGUS109A. Plasmids containing the GATC duplication at the $BamHI_{4837}$ site (BF) were constructed from corresponding "wildtype" plasmids by cutting, Klenow-filling, and religating the BamHI site.

pΩGUS 1162A was constructed via a series of intermediate plasmids. A fragment corresponding to the Ω sequence and 5' end of the GUS coding region was PCR amplified from pAGUS-Tn2 with the primers: 5'GCG GCGGCCGCTAATACGACTCACTATAGGTATTTTTACA AC 3' (SEQ ID No. 3) and 5'TCGCGATCCAGACT-GAATGC 3' (SEQ ID No. 4). Following digestion with NotI (underlined) and NcoI (internal), the amplified fragment was cloned into NotI-NcoI-cut pSL1180 (Pharmacia) giving rise to pSLΩ2. Intermediate plasmid pSLΩGUSA, was constructed by subcloning the GUS gene and poly(A) tail from pVecGUSA into the NcoI and EcoRI sites of pSLΩ2. The Csp45I-EcoRI fragment of pGUS1162A was cloned into similarly-cut pSLΩGUSA, resulting in pΩGUS1162A. To construct pΩGUS109A, GUS along with the $A_{30}$ fragment was cut out from pVecGUSA with NcoI and EcoRI, and cloned into NcoI-EcoRI-cut pSLΩ2.

Plasmids having the 109 nt 3'TE at the 5' end of the GUS gene in place of the wildtype BYDV-PAV 5'UTR are called p109GUSA and p109BFGUSA, respectively (FIG. 1A). pT7 GUS1 (Wang and Miller, 1995) was digested with NcoI at the GUS start codon, filled in with Klenow fragment and then digested with EcoICRI 3' of the stop codon. The 1.8 kb fragment containing the GUS coding sequence was ligated to SmaI cut pTE or pTEBF, giving rise to p109GUS and p109BFGUS, respectively. The EcoRI site in these two constructs was mutated by Klenow fragment fill-in. Then the Csp45I (in the coding sequence of GUS)-ScaI(in the Ampicllin resistance (bla) gene of the vector) fragment was replaced with the corresponding fragment from pPGUS109A, giving rise to p109GUSA and p109BFGUSA, respectively, so that the poly(A) tail was added at the 3' end of GUS gene. The plasmids were digested with XbaI to synthesize the 109GUS and 109BFGUS RNAs. They were cut with EcoRI to synthesize the 109GUSA+ and 109BFGUSA+ RNAs.

EXAMPLE 9

RNA synthesis

The plasmids were digested at appropriate sites as indicated in FIG. 7A. Uncapped transcripts were synthesized with Megascript kit (Ambion, Tex.). Capped transcripts were synthesized with T7 Message mMachine (Ambion, Tex.). RNA concentrations were determined spectrophotometrically. RNA integrity was verified by 1% agarose gel electrophoresis.

EXAMPLE 10

In vitro translation

Subsaturating amounts (0.2 pmole) of capped or uncapped transcripts were translated in wheat germ extracts (Promega). Protein products were quantitated using a Molecular Dynamics Phosphorimager and ImageQuant 3.0 software. In competition experiments, the competitor, either 3'TE RNA or 3'TEBF RNA, was first incubated with the wheat germ extract at room temperature for 5 minutes before the tested mRNA was added to the translation reaction.

EXAMPLE 11

RNA electroporation in protoplasts and GUS assay

Oat (*Avena sativa,* cv. Stout) protoplasts were prepared, electroporated with RNA and cultured. GUS reporter gene assays were performed, except that 30 pmol (subsaturating amounts) of the indicated transcripts were used instead of DNA. Cells were assayed for GUS activity 20 hr after electroporation except in the time course experiment.

EXAMPLE 12

Northern blot hybridization

RNA from electroporated oat protoplasts were isolated and 5 μg of RNA was subjected to electrophoresis. $^{32}P$-labeled antisense GUS gene RNA transcribed from pVec-GUS using SP6 polymerase was used as probe.

EXAMPLE 13

Localization of minimal 3'TE sequence

A 500 base region in the genomic RNA of BYDV-PAV was shown to facilitate translation of uncapped mRNA in vitro. Further, a smaller portion of this region stimulates translation of uncapped mRNA. The mRNAs are in vitro transcripts containing the *E. coli uidA* (GUS) reporter gene flanked by various 5' and 3' UTRs (FIG. 7A). Uncapped GUS mRNA that contains the 109 nt sequence spanning the intergenic region between BYDV-PAV ORFs 5 and 6 in its 3' UTR (bases 4817–4925 of the BYDV-PAV genome) was translated with the same efficiency in vitro as transcripts that contain the larger (500 nt) 3'TE sequence (FIG. 7B, lanes 3–5). This construct yielded more than 50-fold more GUS protein than transcripts lacking the intercistronic sequence (FIG. 7B, compare lanes 2 and 3). Deletion of bases upstream of nucleotide (nt) 4837 (Wang and Miller, 1995) or downstream of nt 4873 within the 3'TE abolished stimulatory activity. Therefore, a subset (bases 4817–4925) of the 500 base fragment is sufficient to confer translation enhancement of uncapped mRNA in a wheat germ extract. This 109 nucleotide sequence as the in vitro-defined, or 109 nt 3'TE.

To confirm the specificity of the stimulation by the 3'TE, a mutation was introduced by inserting a four base duplication (GAUC) within the $BamHI_{4837}$ site in the 3'TE (PGUS109BF; all clones with the BF designation contain this BamHI-fill-in mutation). This duplication abolished the stimulatory activity of the 3'TE (FIG. 7C, compare lanes 4 and 6). Addition of a 5' cap rescued translation of these mutant transcripts to the level observed for uncapped, 3'TE-containing PGUS109 (FIG. 7C, lane 4 and 5). The presence of a poly(A) tail had little effect on translation of any transcripts in wheat germ extracts (FIG. 7C).

EXAMPLE 14

Activity of the 3'TE in vivo

To assess the activity of the 3'TE in vivo, GUS-encoding transcripts with various 5' and 3'UTRs were electroporated into oat protoplasts and translational efficiency was measured by assaying for GUS activity. An uncapped control transcript, containing a plasmid-derived 5' UTR and a 30 nt poly(A) tail yielded no significant GUS activity (FIG. 2A, VecGUSA+). When capped, this mRNA expressed GUS at 50-fold above background, consistent with the essential role for the 5' cap. Replacement of the plasmid-derived 5' UTR with that from BYDV-PAV stimulated GUS expression from capped mRNA 3-fold further (FIG. 8A, PGUSA+). Addition of the 109 nucleotide, in vitro-defined 3'TE was not sufficient for translation of mRNA in vivo (FIG. 8A, compare PGUS109 and PGUS). Presence of a poly(A) tail in addition to the 109 nt 3'TE resulted in a 10-fold increase above background in GUS expression from uncapped mRNA (FIG. 8A, compare uncapped PGUS109A+with uncapped PGUS109). However, addition of a 5' cap to this transcript stimulated GUS expression by another order of magnitude (FIG. 8, compare capped and uncapped PGUS109A+). Construct PGUS109BFA+, which contains the four base GAUC duplication, yielded no GUS activity when lacking a cap, but was fully active when capped (FIG. 8A). These results show that the 109 nt 3'TE only partially, but significantly, facilitated cap-independent translation in vivo.

The effect of additional viral sequence in the 3' UTR on 3'TE function in vivo was examined. PAV bases 4,515 to 5,677 (the 3'-terminal 1162 bases of the genome) were placed in the 3'UTR of the GUS reporter construct. Uncapped transcript from this plasmid gave activity >100-times background (FIGS. 8A,B, PGUS1162). Addition of a cap stimulated expression no more than two-fold (FIGS. 8A,B, compare capped and uncapped PGUS1162). The four base duplication in the $BamHI_{4837}$ site abolished expression from uncapped transcript both in vitro (FIG. 8C, lanes 2 and 4) and in vivo (FIG. 8B, compare uncapped PGUS1162BF with uncapped PGUS1162), verifying the specificity of the 3'TE effect. Furthermore, the four base duplication had no effect on expression of the capped transcript (FIG. 8B, compare capped PGUS1162BF with capped PGUS1162). Interestingly, the stimulatory activity of the 1162 nt 3'end of BYDV-PAV sequence did not require a poly(A) tail (FIG. 8B, compare PGUS1162 and PGUS1162A+). Thus, sequence(s) different from the 3'TE functionally substitutes for a poly(A) tail. In addition, full stimulation of cap-independent translation requires more viral sequence in vivo than in vitro. Because of this difference, the 3'TE is functionally defined as the sequence that stimulates cap-independent translation from the 3'UTR and is rendered nonfunctional by mutation at the BamHI site.

All the results above were obtained from RNA transcripts harboring the 5'UTR from BYDV-PAV (indicated by the "P" preceding "GUS" in the transcript name). The requirement for the 5'UTR from BYDV-PAV RNA was examined by replacing it with the 5'UTR (Ω sequence) of TMV RNA. This sequence stimulates translation in vitro (with or without a cap) and in vivo in a highly cap-dependent manner. Substitution of the BYDV-PAV 5' UTR with Ω permitted a low rate of translation of uncapped mRNA in vitro (FIG. 8C, lane 8). However, Ω in place of the BYDV-PAV 5' UTR abolished translation of uncapped mRNA in vivo, even in the presence of the 1162 nucleotide virus-derived 3' UTR (FIG. 8B, (GUS 1162), but permitted efficient translation of capped (GUS 1162 RNA. Thus, Ω facilitates translation in a cap-dependent manner only and does not cooperate with the 3'TE to promote cap-independent translation. Previously, a vector-derived 5'UTR also failed to support 3'TE activity in vitro. Thus, the 3'TE probably requires at least a portion of the BYDV-PAV 5' UTR for cap-independent translation in these contexts, indicating specific interactions between the 3' and 5'UTR.

The fact that expression of the capped, poly(A)+, Ω-containing mRNA which is considered to be an optimal plant message, is no higher than that of uncapped mRNA containing the full BYDV-PAV 5' and 3' UTRs (FIG. 8B, compare uncapped PGUS1162 and capped (GUS1162A+), demonstrates the very high levels of expression that are conferred by this cap-independent translation signal.

EXAMPLE 15

The 3'TE mimics a 5' cap in its effect on RNA stability

It is possible that the 3'TE stimulates gene expression in vivo, at least in part, by increasing RNA stability. However, the 109 nt 3'TE did not affect RNA stability in wheat germ extracts. To determine the effect of the larger, in vivo-defined 3'TE on RNA stability in vivo, RNA transcripts with wild-type or mutant (the four base duplication) 1162 nt 3'UTR were electroporated into oat protoplasts under the same conditions as the GUS gene expression experiments, and RNA degradation was monitored by northern blot hybridization. The RNA transcripts with either the wild type or the defective 3'TE did not differ significantly in degradation rate (FIG. 9A).

Northern blot hybridization detects only the physical stability of total cellular GUS mRNAs, and cannot discriminate between translatable and untranslatable RNAs. As a more accurate assay of RNA stability, the functional RNA half life was measured by the kinetics of GUS synthesis. The activity of GUS (a very stable enzyme) should stop increasing sooner for a functionally unstable mRNA than for a stable one. Of the three mRNAs for which GUS activity was detectable, none leveled off until at least 30 hr after electroporation (FIG. 9B). This is beyond the 20 hr timepoint used in FIG. 8. Uncapped PGUS1162 mRNA appeared to be slightly less stable than its capped counterpart, but showed a very similar stability (shape of curve) to the capped P1162BF mutant. Thus, the capped mRNA with the defective 3'TE (PGUS 1162BF), and uncapped mRNA containing active 3'TE (PGUS1162) have similar "functional" stabilities, suggesting that the 3'TE either has no role in stabilizing mRNA, or that it contributes a similar amount to stability as the presence of a 5' cap. The similar physical stability of uncapped PGUS1162 and uncapped PGUS1162BF (FIG. 9A), but dramatic differences in GUS gene expression (FIG. 9B), indicate that the 3'TE functions at the translational level.

EXAMPLE 16

The 3'TE decreases the requirement of eIF4F for efficient translation of uncapped mRNA One possible role of the 3'TE in enhancing translation of uncapped mRNA is to efficiently recruit essential initiation factor(s) that facilitate(s) binding of the ribosomal small subunit, in a manner analogous to that of the 5' cap of mRNAs. The binding of eIF4F to the 5' cap structure confers the selective translation of capped, as opposed to uncapped, mRNA. The translation enhancing sequence from STNV RNA dramatically decreased the amount of the rate-limiting initiation factor, eIF4F, required for maximal translation efficiency in vitro. The eIF4F requirements of mRNAs containing or lacking the 3'TE were compared. The already efficient translation of capped 3'TE-lacking mRNA, and uncapped mRNA containing the 109 nt 3'TE was not stimulated by exogenous eIF4F (FIG. 10, lanes 1–10). Consequently, eIF4F was not rate-limiting for these mRNAs. In contrast, the endogenous eIF4F levels were rate-limiting for uncapped mRNA with the defective 3'TE, because translation efficiency of this mRNA increased correspondingly with the addition of exogenous eIF4F (FIG. 10, lanes 11–15). As a control, bovine serum albumin was added instead of eIF4F, and was observed to have no effect on translation of any mRNAs (data not shown). Thus, the 109 nt 3'TE appears to reduce the amount of of eIF4F required for efficient translation, a property that is normally conferred by a 5' cap.

EXAMPLE 17

The 109 nt 3'TE inhibits translation of mRNAs in trans by a mechanism that is reversed by exogenous eIF4F If the 3'TE enhances translation by efficiently recruiting eIF4F, either directly or via an unidentified trans-acting factor, the 3'TE-dependent or cap-dependent translation would be inhibited by the 3'TE in trans. The free 3'TE RNA should act as a competitor for eIF4F or other factors that mediate 3'TE stimulation in cis. To test this, a 109 nt transcript comprising only the in vitro-defined 3'TE RNA was added in excess to wheat germ extracts containing various mRNAs. Indeed, translation of uncapped 3'TE-plus mRNA (PGUS109) was inhibited by the addition of 3'TE RNA (FIG. 11A, lanes 1–4). Addition of the defective 3'TE that differs only by having the GAUC duplication (3'TEBF) had no inhibitory effect (FIG. 11A, lanes 5–7). This shows that the inhibition by wildtype 109 nt 3'TE was not simply a nonspecific effect of adding RNA to the wheat germ extract. Addition of eIF4F to the reaction reversed the trans-inhibition by the 3'TE (FIG. 11A, lanes 8–12). Thus, either the 3'TE-mediated cap-independent translation requires eIF4F, or the mechanism is normally eIF4F-independent and added eIF4F allows translation of PGUS109 to bypass the 3'TE-mediated mechanism. To distinguish between these possibilities, the effect of the 3'TE on translation of capped mRNA lacking any BYDV-PAV sequence was examined. Excess added wildtype 3'TE RNA inhibited translation of capped mRNA containing (as its 5'UTR (FIG. 5B, lanes 1–5). Again, the defective 3'TEBF RNA had no effect on the translation of this capped mRNA (FIG. 11B, lanes 6–9), and addition of eIF4F restored translation of (GUS mRNA in the presence of inhibitory levels of 3'TE (FIG. 11B, lanes 10–14). Thus, the 109 nt 3'TE competes with capped mRNA for factor(s) required for cap-dependent translation and does not need to interact with the BYDV-PAV 5'UTR to do so. The restoration of translatability of both mRNAs in the presence of inhibitory levels of 3'TE by eIF4F strongly implicates a role, either direct or indirect, for eIF4F in cap-independent translation mediated by the 3'TE in cis.

EXAMPLE 18

The 109 nt 3'TE functions in the 5' UTR

The 3'TE functionally mimics a 5' cap. If this is the case, like the cap, the 3'TE should function in the 5'UTR. Hence, the 109 nt 3'TE was moved to the 5' end of the GUS gene in place of the BYDV-PAV 5'UTR (construct 109GUSA). This mRNA was translated cap-independently (FIG. 12A, lanes 3 and 4). In contrast, the nearly identical construct, 109BFGUS, differing only by the GAUC duplication, was not translated in a cap-independent manner (FIG. 12A, compare lanes 6 and 4). Capped mRNAs, even with the nonfunctional 3'TE at the 5'UTR, were still translated efficiently (FIG. 12A, compare lanes 5 and 3), similar to the results seen when the mutant 3'TE was located at the 3'UTR (FIG. 7C). Furthermore, in trans, free 109 nt 3'TE (but not the defective mutant form) inhibited translation of uncapped mRNA that contained the 109 nt 3'TE at the 5'UTR (FIG. 12B).

To show the function of the 5'-located 3'TE in vivo, polyadenylated transcripts containing wildtype or defective 3'TE in the 5'UTR were electroporated into oat protoplasts. The wildtype 109 nt 3'TE, but not the mutant, 3'TE stimulated GUS expression to a level 30-fold greater than background (FIG. 12C, compare uncapped 109BFGUSA+ with uncapped 109GUSA+). Addition of a 5' cap stimulated translation another seven-fold, similar to what was observed when the 109 nt 3'TE was located in the 3'UTR (FIG. 8A, PGUS109A+). As a control, a construct also lacking the BYDV-PAV 5'UTR, but with the 109 nt 3'TE in the 3'UTR ((GUS109A+) gave no GUS expression unless capped. This is not surprising, because a similar construct but with the full 1162 nt 3'UTR from BYDV-PAV (ΩGUS1162) also showed no cap-independent translation. The 1162 nt 3'UTR (full, in vivo-defined 3'TE) could not be tested in the 5'UTR owing to the presence of numerous AUG codons. Interestingly, the 5'-located 109 nt 3'TE stimulated translation of uncapped mRNA to a level that was nearly one-half that of uncapped PGUS1162 in protoplasts (FIG. 12C). When located in the 3'UTR, the 109 nt 3'TE (PGUS109A+) gave expression that was only about one-eighth that of PGUS1162 (FIG. 8A). Thus, the 3'TE may stimulate translation more efficiently from the 5'UTR. Most importantly, FIG. 12 shows that interaction between the natural viral 5'UTR and 3'TE is not essential for recruitment of the translation machinery that gives cap-independent translation.

EXAMPLE 19

A highly conserved portion of the 3'TE in other plant viral genomes

To determine how widespread this 3' translation enhancer phenomonon might be, a BLAST search of the Genbank database was performed for homologous sequences. A 27 base sequence that spans the BamHI site and is absolutely conserved in all eleven sequenced BYDV-PAV and BYDV-MAV isolates (Chaloub et al., 1994), was used as the sequence for comparison. An 18 nucleotide portion of this sequence was discovered to be conserved near the 5' ends of the 3' UTRs of all subgroup I luteovirus genomes, RNA's 1 of the bipartite dianthoviruses, and tobacco necrosis virus RNA (TNV, the helper for STNV), but not STNV RNA (FIG. 13). This suggests that these other viruses may employ this mechanism of translation. TNV RNA is known to lack a 5' cap, but RCNMV RNA1 is reportedly capped. As expected, BYDV-PAV RNA also appears to lack a cap, and in vitro transcripts of a full-length clone of the BYDV-PAV genome are more infectious when lacking a 5' cap. The presence of a highly conserved sequence at similar locations in the viral genomes, combined with the fact that this sequence contains the BamHI site, mutation of which destroys 3'TE function, suggests that the 18 base sequence in FIG. 13 is directly involved in the mechanism of cap-independent translation.

EXAMPLE 20

The 3'TE mimics a 5' cap, not a poly(A) tail

The 109 nt intergenic region (109 nt 3'TE) between ORFs 5 and 6 of the BYDV-PAV genome confers a remarkably high (30 to 100-fold) stimulation of translation of uncapped mRNA in wheat germ extracts. The complete abolition of the 3'TE stimulatory activity by a small mutation (4 base duplication) within this sequence demonstrates the high sequence specificity of the interaction between the mRNA and some component of the translational apparatus. However, the 109 nt 3'TE sequence alone was insufficient for full stimulation in vivo, even in the presence of a poly(A) tail. Poly(A) tails have little influence on translation in wheat germ extracts, but interact with the 5' cap to facilitate translation in vivo. The endogenous levels of GUS activity in oat cells obscured any low level of translation that might have been obtained from reporter mRNAs lacking both a 5' cap and the 3'TE, or both a poly(A) tail and the 1162 nt viral 3' UTR. This large portion of the BYDV-PAV genome that spans the smaller in vitro-defined 3'TE was required to stimulate translation of uncapped mRNA to a level of at least one-half of its capped counterpart in vivo. Because this sequence obviated the need for a poly(A) tail, the large 3'UTR may also contain a sequence that functionally substitutes for a poly(A) tail such as the pseudoknot-rich domain of TMV, and the 3' stem-loop of histone mRNAs. This poly(A) tail-like activity is functionally distinct from the cap-like activity of the 3'TE as evidenced by the BamHI fill-in mutant which had no 3'TE activity but full translation activity in vivo when capped (FIG. 8B, PGUS1162BF).

Measurement of the RNA degradation rate in wheat germ (Wang and Miller, 1995) and in vivo (FIG. 3) indicated that there is no significant difference in the stability of uncapped RNA containing the full, in vivo-defined 3'TE (PGUS1162) and capped 3'TE-mutant (PGUS1162BF) transcripts. In one of the main eukaryotic decay pathways, cellular mRNAs are deadenylated first, followed by decapping and degradation in a 5' to 3' direction. Because decapped mRNAs are degraded rapidly in vivo, the additional viral sequence needed for the 3'TE to function in vivo, but not in vitro, may serve to confer RNA stability. It may do this simply by recruiting translational machinery so efficiently that the mRNA is inaccessible to nucleases. mRNAs undergoing effecient translation are associated with poly(A) binding protein, eIF4F and other translation factors to form a circular mRNP structure, and thus they should be more resistant to the 5' exonuclease attack. The 3'–5' communication required for 3'TE function (in its normal 3'UTR setting) may exploit the factors that mediate the poly(A) tail-5' cap interactions in such a way as to prevent recognition by the exonucleases that target uncapped or nonpolyadenylated mRNAs.

To summarize, the 3'TE of PAV RNA has all the following properties of a 5' cap: (1) It eliminates the need for a 5' cap for efficient translation in vitro and in vivo (in conjunction with the 5'UTR). (2) It can be replaced by a 5' cap. (3) It cannot be replaced by a poly(A) tail. (4) It requires a poly(A) tail or viral 3'UTR sequence for translation in vivo but not in wheat germ extracts. (5) It stabilizes mRNA to the same extent as a 5' cap in vivo. (6) It reduces the concentration of eIF4F needed for maximum translation. (7) Its activity is inhibited by added free $m^7G$ (Wang and Miller, 1995) or free 109 nt 3'TE in trans (FIG. 11). (8) Free $m^7G$ or free 109 nt 3'TE inhibit translation of capped mRNAs lacking any BYDV-PAV sequence. (9) All types of inhibition above are relieved by exogenous eIF4F. (10) The 109 nt 3'TE functions when located at the 5' end of mRNA. This last observation makes the important distinction between the two functions that are mediated by the 3'TE: translation initiation (e.g ribosome recruitment), and 3'–5' communication.

EXAMPLE 21

3'–5' communication

When the 3'TE is located at the 3' end of the mRNA, interaction between the 5' and 3' ends must occur, given that ribosomes scan 5' to 3' and peptide synthesis initiates at the 5' proximal AUG. The specific involvement of the BYDV-PAV 5'UTR in this interaction was suggested by the result that neither a vector-derived 5'UTR (Wang and Miller, 1995), nor the translationally efficient 5'UTR (Ω) of TMV supported 3'TE function. However, one cannot rule out the possiblity that other 5'UTRs might also function. The interaction between the 3'TE and 5'UTR of BYDV-PAV RNA could be through either long-distance basepairing as proposed for STNV or mediated via trans-acting factor(s). The first possibility is unlikely for BYDV-PAV. First, computer analysis revealed no strong, conserved Watson-Crick basepairing between the 5' and 3' UTRs. Secondly, the 3'TE functions at widely varying distances from the 5' UTR and tolerates unrelated (GUS or viral) intervening sequences, which would be expected to affect such long distance basepairing. Thirdly, the 3'TE can trans-inhibit translation of capped (GUS mRNA lacking any BYDV-PAV sequence, arguing against specific base-pairing as a mechanism for inhibition. Instead, the 3'TE most likely interacts with a factor (or the ribosome itself) required for translation of all capped mRNAs, in order to facilitate the interactions between 3' and 5' UTRs. One possiblity is that a trans-acting factor first recognizes the 3' TE and then interacts with an initiation factor, such as eIF4F, which in turn interacts with the 5' end. This would resemble the interaction between eIF4F and poly(A) binding protein as in normal poly(A) tail-mediated translation initiation, with the crucial difference that a 5' cap is not needed for 5' end recognition. Other proteins are known to interact functionally with both ends of mRNAs, but also in a cap-dependent manner.

EXAMPLE 22

Ribosome recruitment

Some of the same components proposed for 3'–5' communication may also be involved in ribosome recruitment. The simplest model would be that eIF4F has a high affinity for the 3'TE (FIG. 14A). A structure within the 3'TE may mimic a 5' cap to recruit the eIF4E subunit of eIF4F, or the 3'TE may bind eIF4G. The latter case would resemble IRES-mediated cap-independent translation in which eIF4G was found to bind the functional IRES RNA with much higher affinity than defective mutant IRES RNAs, or non-IRES RNA. Of course the IRES differs from the 3'TE by having the binding site located in the 5'UTR. eIF4F as well as eIF4B have been reported to bind poly(A) tails directly or via poly(A) binding protein in order to facilitate initiation at the 5' AUG. Although these interactions require a cap for 5' end recognition, the same protein(s) may facilitate the 3'–5' communication that allows the 3'TE and viral 5'UTR to facilitate initiation at the 5' end in the absence of a cap.

The second model invokes an unknown factor that specifically binds the 3'TE and possibly also the 5'UTR prior to recruiting eIF4F (FIG. 14B). The trans-inhibition of translation by the 3'TE, as well as reversal of trans-inhibition by eIF4F could be explained by the 3'TE RNA interacting with the unknown trans-acting factor which then binds eIF4F. This resembles yeast poly(A) binding protein Pab1p which binds eIF4F only in the presence of poly(A).

A third, different possibility which can act in addition to, or instead of, one of the previous models, is that the 3'TE may base-pair directly to 18S ribosomal RNA. This would resemble bacterial mRNA-ribosome binding (Shine-Dalgarno) interactions. The highly conserved 18 base tract in the 3'TE contains the sequence GAUCCU (underlined in FIG. 13). This sequence has the potential to base-pair to a region in 18S ribosomal RNA that is precisely the same number of bases from the 3' end as the prokaryotic message binding site (anti-Shine-Dalgarno sequence) in 16S rRNA. Thus, ribosome binding may occur by a prokaryotic-like mechanism as proposed for ribosomal recognition of picornaviral IRES's, ribosome jumping on adenovirus mRNAs, and ribosome binding of STNV RNA (FIG. 14C). eIF4F may facilitate this or eIF4F may simply bind after the event to promote 5' end recognition and 5' to 3' scanning to the initiator AUG. In support of this model, the lethal GAUC duplication includes four of the six bases in the potential rRNA-binding sequence (FIG. 13). The duplication may disrupt 3'TE-18S rRNA interactions, for example by altering secondary structure (FIG. 14C). The homologous sequence in the apparently capped RNA1 of RCNMV has a mismatch in this six base sequence. Deletion of this homologous sequence did not greatly reduce translation of uncapped RCNMV RNA1 transcript.

The 18 base sequence is conserved poorly if at all in the 3' UTR of STNV RNA, but computer alignment of part of the stimulatory region of the STNV 3' UTR with the above viral RNAs also aligns the proposed rRNA binding sequences (FIG. 13). However, the STNV sequence identified by Danthinne et al. (1993) would base-pair to a region much further from the 3' end of 18S rRNA and requires disruption of a very stable stem-loop in the rRNA. Danthinne et al. (1993) also proposed that the 3' stimulatory sequence enhances translation by binding ribosomes that have completed translation to facilitate rapid recycling to the 5' end. This mechanism is ruled out in the case of BYDV-PAV RNA by the ability of the 3'TE to function when located in the 5'UTR and absent from the 3'UTR. Whatever the mechanism, it is clear that resolving the mechanism(s) of cap-independent translation initiation conferred by the BYDV-PAV 3'TE will broaden understanding of the possibilities for translation initiation in eukaryotes.

EXAMPLE 23

Cap-Independent Translation In Yeast

The 3' translation enhancer (3'TE) also confers cap-independent translation in yeast. Yeast spheroplasts (cells with walls removed) were electroporated with GUS mRNAs. Maps of these constructs and the GUS assay methods are as disclosed above.

| | Fluorescence units (GUS Activity) | |
|---|---|---|
| RNA | Uncapped | Capped |
| None | 7 | — |
| PGUS1162 | 54 | 144 |
| PGUS1162BF | 12 | 86 |

PGUS1162 has the full 3' end of BYDV-PAV RNA that gave full stimulatory activity in plant cells. BF indicates the same construct but with the four base GAUC duplication at the BamHI site in the 3'TE that destroys its function in vitro and in plant cells.

The 3'TE also functions in an in vitro translation system derived from yeast that is poly(A) tail-dependent and accurately represents the in vivo situation, in terms of the effects of 5' cap and poly(A) tail. This was done using the luciferase (LUC) reporter gene instead of GUS.

| | Luminescence units (LUC Activity) | |
|---|---|---|
| RNA | Uncapped | Capped |
| None | 0 | — |
| PLUC1162 | 7.8 | 55.5 |
| PLUC1162BF | 0 | 14.8 |

The 7.8 units of LUC activity is significantly above background which is 0. This effect has not been demonstrated previously with other uncapped, nonpolyadenylated mRNAs. Note that the construct that differs only by the BF mutation, has no translation activity, as would be expected.

The 3'TE can be used with a poly(A) tail in yeast to boost expression substantially. If this or other optimization gives significant expression in yeast, then the sequence would work in all eukaryotes (plants, animals and fungi).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of producing a protein translated from an uncapped eukaryotic messenger ribonucleic acid (mRNA) in a eukaryotic cell, comprising the steps of:

selecting an RNA with a nucleotide sequence encoding a protein to be expressed;

joining nucleotides 1–168 of the barley yellow dwarf virus RNA, PAV serotype, to the 5' untranslated region of said uncapped mRNA, said nucleotides 1–168 comprising the 5' untranslated region plus first 27 nucleotides of the open reading frame of the barley yellow dwarf virus RNA;

linking nucleotides 4513–5677 of the barley yellow dwarf virus RNA, PAV serotype, to the 3' untranslated region of said uncapped mRNA; and introducing said uncapped mRNA into said eukaryotic cell.

2. The method of claim 1, wherein said uncapped eukaryotic mRNA is selected from the group consisting of those coding for peptide hormones, vaccines, antibodies, enzymes, altered seed storage proteins, insect toxins, and disease resistance genes.

3. A DNA molecule which comprises:

(a) a promoter region which functions in plant cells to cause the production of an RNA sequence, which is operably linked to (b) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA;

(c) a coding sequence, wherein said coding sequence is heterologous to said 5' untranslated region, which is operably linked to (d) a 3' untranslated region that functions in plant cells to cause the termination of transcription, said 3' untranslated region comprising nucleotides 4513–5677 of the barley yellow dwarf virus RNA.

4. The DNA of claim 3, wherein said promoter region is selected from the group consisting of a promoter region from a bacteriophage requiring a corresponding bacteriophage RNA polymerase, a promoter region for RNA polymerase III, and a promoter region for RNA polymerase I.

5. The DNA of claim 4, wherein said coding sequence is selected from the group consisting of those coding for peptide hormones, vaccines, antibodies, enzymes, altered seed storage proteins, insect toxins, and disease resistance genes.

6. A method for providing gene expression in plants which comprises:

(a) transforming plant cells with a DNA molecule which comprises:

(i) a promoter region which functions in plant cells to cause the production of an RNA sequence, which is operably linked to (ii) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus first 27 nucleotides of the open reading frame of the barley yellow dwarf virus RNA;

(iii) a coding sequence, wherein said coding sequence is heterologous to said 5' untranslated region, which is operably linked to (iv) a 3' untranslated region that functions in plant cells to cause the termination of transcription, said 3' untranslated region comprising nucleotides 4513–5677 of the barley yellow dwarf virus RNA;

(b) selecting said plant cells which have been transformed;

(c) regenerating said plant cells to provide a differentiated plant; and (d) selecting a transformed plant which expresses said gene.

7. A method of producing a protein translated from an uncapped eukaryotic messenger ribonucleic acid (mRNA) in a eukaryotic cell, comprising the steps of:

selecting an RNA with a nucleotide sequence encoding a protein to be expressed;

joining nucleotides 4817–4925 of the barley yellow dwarf virus RNA, PAV serotype, to the 5' untranslated region of said uncapped mRNA; and introducing said uncapped mRNA into said eukaryotic cell.

8. The method of claim 7, wherein said uncapped eukaryotic mRNA is selected from the group consisting of those coding for peptide hormones, vaccines, antibodies, enzymes, altered seed storage proteins, insect toxins, and disease resistance genes.

9. A DNA molecule which comprises:

(a) a promoter region which functions in plant cells to cause the production of an RNA sequence, which is operably linked to (b) a 5' untranslated region including a 5' translation enhancing segment, said 5' translation enhancing segment comprising nucleotides 4817–4925 of the barley yellow dwarf virus RNA, PAV serotype;

(c) a coding sequence, wherein said coding sequence is heterologous to said 5' untranslated region, which is operably linked to (d) a 3' untranslated region that functions in plant cells to cause the termination of transcription.

10. The DNA of claim 9, wherein said promoter region is selected from the group consisting of a promoter region from a bacteriophage requiring a corresponding bacteriophage RNA polymerase, a promoter region for RNA polymerase III, and a promoter region for RNA polymerase I.

11. The DNA of claim 10, wherein said coding sequence is selected from the group consisting of those coding for peptide hormones, vaccines, antibodies, enzymes, altered seed storage proteins, insect toxins, and disease resistance genes.

12. A method for providing gene expression in a eukaryotic cell which comprises:

(a) transforming eukaryotic cells with a DNA molecule which comprises:

(i) a promoter region which functions in said eukaryotic cells to cause the production of an RNA sequence, which is operably linked to (ii) a 5' untranslated region including a 5' translation enhancing segment, said 5' translation enhancing segment comprising nucleotides 4817–4925 of the barley yellow dwarf virus RNA, PAV serotype;

(iii) a coding sequence, wherein said coding sequence is heterologous to said 5' untranslated region, which is operably linked to (iv) a 3' untranslated region that functions in said cells to cause the termination of transcription;

(b) selecting said eukaryotic cells which have been transformed; and (c) selecting a transformed host which expresses said gene.

13. The method of claim 12, wherein said cell is selected from the group consisting of a plant cell, an animal cell and a fungal cell.

14. A method for expressing a gene in a plant which comprises:

(a) producing a plant, the cells of said plant comprising a DNA molecule which comprises:

(i) a promoter region which functions in plant cells to cause the production of an RNA sequence, which is operably linked to (ii) a 5' untranslated region including a 5' translation enhancing segment, said 5' translation enhancing segment comprising nucleotides 1–168 of the barley yellow dwarf virus RNA, PAV serotype, said nucleotides 1–168 encompassing the 5' untranslated region plus the first 27 nucleotides of the open reading frame of the barley yellow dwarf virus RNA;

(iii) a coding sequence, wherein said coding sequence is heterologous to said 5' untranslated region, which is operably linked to (iv) a 3' untranslated region that functions in plant cells to cause the termination of transcription, said 3' untranslated region comprising nucleotides 4513–5677 of the barley yellow dwarf virus RNA.

15. A method for expressing a gene in a plant which comprises:

(a) producing a plant, the cells of said plant comprising a DNA molecule which comprises:

(i) a promoter region which functions in said plant cells to cause the production of an RNA sequence, which is operably linked to (ii) a 5' untranslated region including a 5' translation enhancing segment, said 5' translation enhancing segment comprising nucleotides 4817–825 of the barley yellow dwarf virus RNA, PAV serotype;

(iii) a coding sequence, wherein said coding sequence is heterologous to said 5' untranslated region, which is operably linked to (iv) a 3' untranslated region that functions in said cells to cause the termination of transcription.

* * * * *